US012606590B2

(12) United States Patent
Warminski et al.

(10) Patent No.: US 12,606,590 B2
(45) **Date of Patent: *Apr. 21, 2026**

(54) MRNA 5'-END CAP ANALOGS, RNA MOLECULE INCORPORATING THE SAME, USES THEREOF AND METHOD OF SYNTHESIZING RNA MOLECULE OR PEPTIDE

(71) Applicants: Uniwersytet Warszawski, Warsaw (PL); Explorna Therapeutics Sp. z o.o., Warsaw (PL)

(72) Inventors: Marcin Warminski, Warsaw (PL); Pawel Sikorski, Warsaw (PL); Joanna Kowalska, Warsaw (PL); Jacek Jemielity, Warsaw (PL)

(73) Assignees: Uniwersytet Warszawski, Warsaw (PL); Explorna Therapeutics Sp. z o.o., Warsaw (PL)

( * ) Notice: Subject to any disclaimer, the term of this patent is extended or adjusted under 35 U.S.C. 154(b) by 908 days.

This patent is subject to a terminal disclaimer.

(21) Appl. No.: 17/798,099

(22) PCT Filed: Feb. 12, 2021

(86) PCT No.: PCT/PL2021/050007

§ 371 (c)(1),
(2) Date: Aug. 8, 2022

(87) PCT Pub. No.: WO2021/162567

PCT Pub. Date: Aug. 19, 2021

(65) Prior Publication Data

US 2023/0130423 A1 Apr. 27, 2023

(30) Foreign Application Priority Data

Feb. 12, 2020 (PL) ...................................... P.432883

(51) Int. Cl.

| | |
|---|---|
| ***C07H 21/02*** | (2006.01) |
| ***C12N 15/67*** | (2006.01) |
| ***C12P 19/34*** | (2006.01) |
| ***C12P 21/02*** | (2006.01) |

(52) U.S. Cl.
CPC ............. *C07H 21/02* (2013.01); *C12N 15/67* (2013.01); *C12P 19/34* (2013.01); *C12P 21/02* (2013.01)

(58) Field of Classification Search
CPC .. C07H 21/02; C12N 2310/317; C12N 15/67; C12P 19/34; C12P 21/02
See application file for complete search history.

(56) References Cited

FOREIGN PATENT DOCUMENTS

| | | | |
|---|---|---|---|
| WO | WO2017053297 | A1 | 3/2017 |
| WO | WO2017066797 | A1 | 4/2017 |
| WO | WO2019175356 | A1 | 9/2019 |
| WO | WO2021/162566 | A1 | 8/2020 |

OTHER PUBLICATIONS

Grudzien et al., RNA, Oct. 2004, p. 1479-1487. (Year: 2004).*
Kowalska Joanna et al: "Synthesis and characterization of mRNA cap analogs containing phosphorothioate substitutions that bind tightly to elF4E and D4 are resistant to the decapping pyrophosphatase DcpS", RNA, vol. 14, No. 6, Jun. 1, 2008 (Jun. 1, 2008), pp. 1119-1131.
Pawel J. Sikorski et al. (2020), "The identity and methylation status of the first transcribed nucleotide in eukaryotic mRNA 5 cap modulates protein expression in living cells", Nucleic Acids Research, 2020, vol. 48, No. 4, pp. 1607-1626, published online on Jan. 27, 2020; doi: 10.1093/nar/gkaa032.
Shikawa Masahide et al. (2009), "Preparation of eukaryotic mRNA having differently methylated adenosine at the 5'-terminus and the effect of the methyl group in translation", Nucleic Acids Symposium Series, 53(1), pp. 129-130, (Symposium date: Sep. 27, 2009); doi: 10.1093/nass/nrp065.

* cited by examiner

*Primary Examiner* — Jonathan S Lau
(74) *Attorney, Agent, or Firm* — Arrigo, Lee, Guttman & Mouta-Bellum LLP

(57) ABSTRACT

The invention relates to new mRNA 5' end cap analogs, RNA molecules containing them, their uses and methods for their in vitro synthesis, as well as a method for protein or peptide synthesis in vitro or in cell cultures, which method encompasses translation of the RNA molecule.

14 Claims, 4 Drawing Sheets

MRNA 5'-END CAP ANALOGS, RNA MOLECULE INCORPORATING THE SAME, USES THEREOF AND METHOD OF SYNTHESIZING RNA MOLECULE OR PEPTIDE

TECHNICAL FIELD

This invention relates to novel mRNA 5'-end cap analogs, an RNA molecule incorporating the same, uses thereof and a method of synthesizing the RNA molecule in vitro, as well as a method of synthesizing a protein or peptide in vitro or in cells, said method comprising translating the RNA molecule.

THE STATE OF ART

The 7-methylguanosine cap ($m^7G$) present at the 5' end of eukaryotic mRNA plays an important role in numerous fundamental cellular processes, mainly by protecting mRNA from premature degradation and by serving as a molecular marker for proteins involved in mRNA transport and translation. [1] Therefore, chemical 5' cap modifications pave the way for the design of molecular tools for the selective modulation of cap-dependent processes and, consequently, mRNA metabolism.[2] The presence of 5' cap is needed to control mRNA and its effective translation under normal conditions. Chemically synthesized $m^7GpppG$ cap mRNA analogs are used as in vitro transcription reagents for capped mRNA. [3]

In vitro transcribed (IVT) 5-capped mRNAs are useful tools for studying translation, transport and processing of mRNAs and are an emerging class of promising therapeutic molecules. IVT mRNA finds application in the expression of proteins in eukaryotic cells, extracts, cell cultures and even in whole organisms. Finally, IVT RNA has recently attracted considerable attention as a tool for safe exogenous protein delivery for anticancer vaccination, antiviral vaccination, and gene replacement therapy [4].

The synthesis of 5-capped mRNA using cap analogues can be achieved by in vitro transcription.[3] In this method, called co-transcriptional capping, RNA synthesis is performed by RNA polymerase on a DNA matrix in the presence of all 4 ribonucleoside 5-triphosphates (NTPs: ATP, GTP, CTP, UTP) and a dinucleotide cap such as $m^7GpppG$. The DNA template is designed so that the first transcribed nucleotide is G. Polymerase initiates transcription using GTP or $m^7GpppG$, thereby incorporating one of the nucleotides at the 5' end of the resulting RNA. To increase the percentage of cap analog incorporation (capping efficiency), GTP concentration is reduced relative to other NTPs, and dinucleotide cap concentration is increased (4-10 fold over GTP). Unfortunately, even when using high dinucleotide cap excess over GTP, the capping efficiency is less than 100% and rarely exceeds 90%. Uncapped mRNAs are much less stable and translationally active than capped mRNAs and, moreover, can lead to induction of an unwanted immune response in cells leading to a reduction in translation efficiency also for capped mRNAs [11]. A way to remove uncapped mRNAs is to treat the post-transcriptional mixture with appropriate enzymes (e.g., a mixture of 5'-polyphosphatase and 5'-exonuclease) that degrade uncapped RNA and leave the capped mRNA intact. Another limitation of the mRNA capping method using dinucleotides is the fact that the dinucleotide cap can be reversely incorporated, leading to "Gpppm$^7$G-capped" RNAs that are translationally inactive. This problem was solved by the discovery of 'anti-reverse cap analogs' (ARCAs), which are modified at the 2'- or 3'-positions of 7-methylguanosine (usually by replacing one of the OH groups with an $OCH_3$ group) to block reverse incorporation. [5,6] It has already been shown that the co-transcriptional capping method enables the incorporation of various modified cap structures at the 5' mRNA end. These modified cap structures can be molecular label carriers or give mRNA molecules new properties such as increased translation efficiency and stability. Especially preferred cap analogues are among those modified in the triphosphate bridge. [7] It has been shown that substitution of even one atom in a 5', 5-triphosphate bridge can significantly affect mRNA properties. For example, substitution of a single atom in the β position of the cap oligophosphate bridge, depicted as β-S-ARCA, resulted in a significant increase in mRNA translation efficiency in vitro and in vivo, [8,9] while substitution of a single O atom with a $CH_2$ group at the α-β position resulted in a reduction in translation efficiency. [10] These dramatically different biological effects of different single atom substitutions within the cap indicate for the high sensitivity of the translational machinery to oligophosphate chain modifications and suggest that this is an important area for further exploration.

The objective of the invention is to provide new mRNA 5' end cap analogs that will enable higher transcription efficiency of the mRNA capped with them and a higher level of expression of proteins encoded by such mRNA than those obtained with prior art mRNA 5' end cap analogs. A particular objective of the invention is to provide new mRNA 5' end cap analogs that will enable easy separation of capped and uncapped mRNA present in the in vitro reaction mixture without the need for enzymatic treatment. Unexpectedly, the problem defined above was solved by this invention.

THE DESCRIPTION OF THE INVENTION

An object of the invention is a compound of the formula:

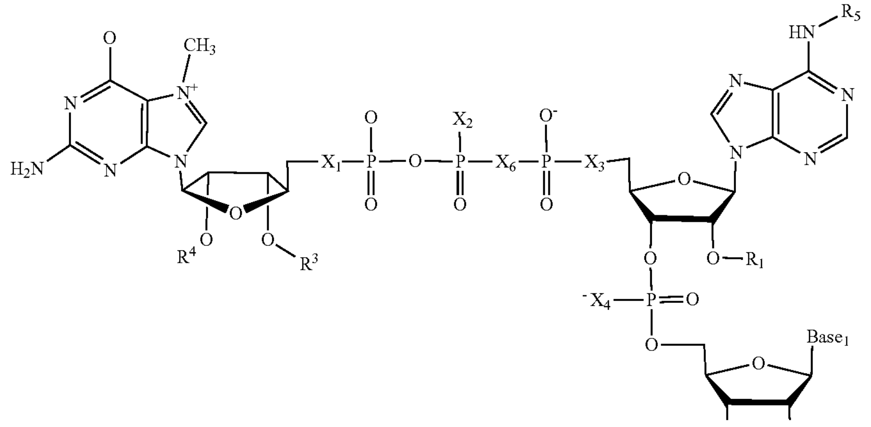

-continued

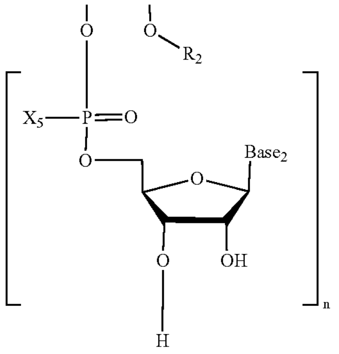

wherein:

$R^1$, $R^2$, $R^3$, $R^4$ are selected from the group consisting of: H, $CH_3$, alkyl, wherein the substituents R with different numbers may be the same or different, n is 0 or 1, $R^5$ is selected from the group consisting of: benzyl, substituted benzyl, especially mono-substituted or di-substituted, preferably with a substituent selected from the group consisting of: chlorine, fluorine, bromine, iodine, methyl group, alkyl, nitro group, carboxyl group, azido group, amino group, hydroxyl group, or any combination thereof, wherein the benzyl may be ortho-, meta- or para-substituted, (1-naphthylmethyl), (2-naphthylmethyl), substituted naphthylmethyl, alkylaryl, aryl, $Base_1$ and $Base_2$ are independently selected from the group including:

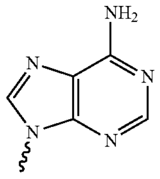

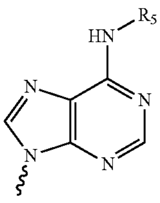

-continued

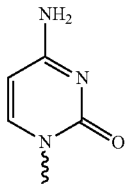

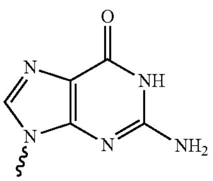

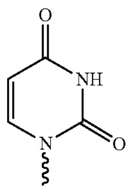

$X^1$, $X^3$, are selected from a group including: O, S, Se, whereby substituents X with different numbers may be the same or different, $X^2$, $X^4$, $X^5$ are selected from the group including: O, S, Se, $BH_3$, wherein the X substituents with different numbers may be the same or different, $X^6$ is selected from the group including: O, $CH_2$, $CF_2$, $CCl_2$, Preferably $R^5$ is benzyl, mono-substituted benzyl, di-substituted benzyl, 1-methylnaphthyl or 2-methylnaphthyl; $X^1$, $X^4$, $X^5$, $X^6$ are O, $X^2$ and $X^3$ are O or S, and $R^3$, $R^4$ are H.

In a preferred embodiment, $R^5$ is selected from the group consisting of: benzyl, chlorobenzyl, fluorobenzyl, bromobenzyl, iodobenzyl, methylbenzyl, alkylbenzyl, nitrobenzyl, carboxybenzyl, azidobenzyl, aminobenzyl, hydroxybenzyl, difluorobenzyl.

Preferrably, this compound was selected from a group including:
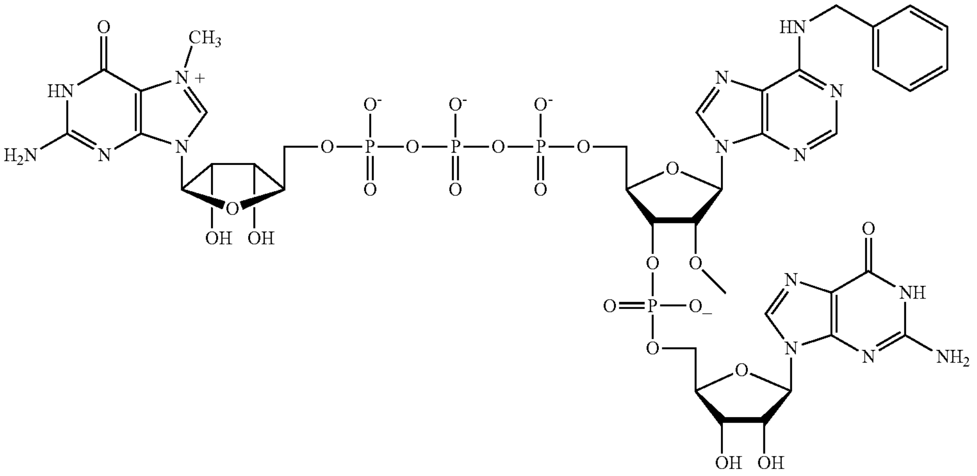
compound $m^7Gppp^{Bn6}A_mpG$ of formula
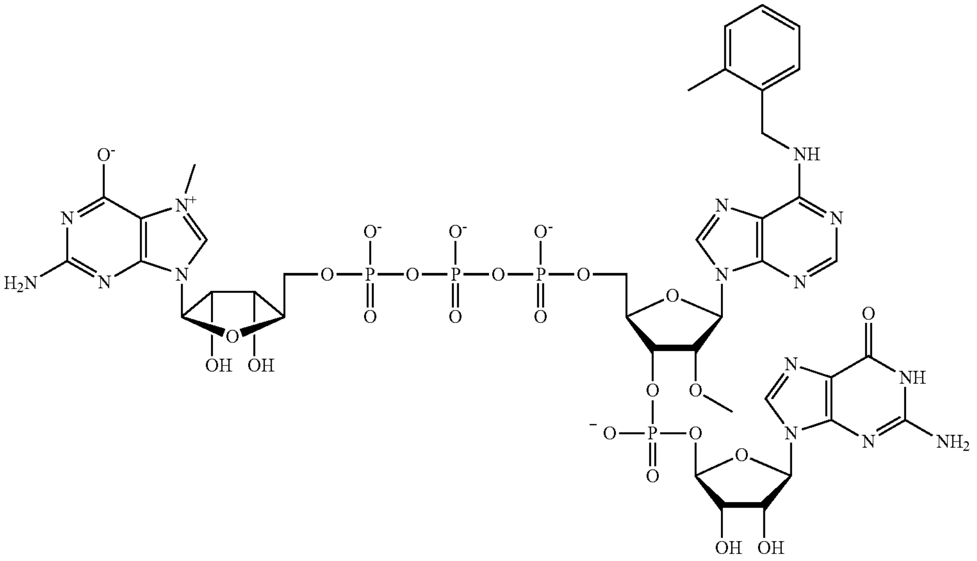
compound $m^7Gppp^{2MeBn6}A_mpG$ of formula -continued
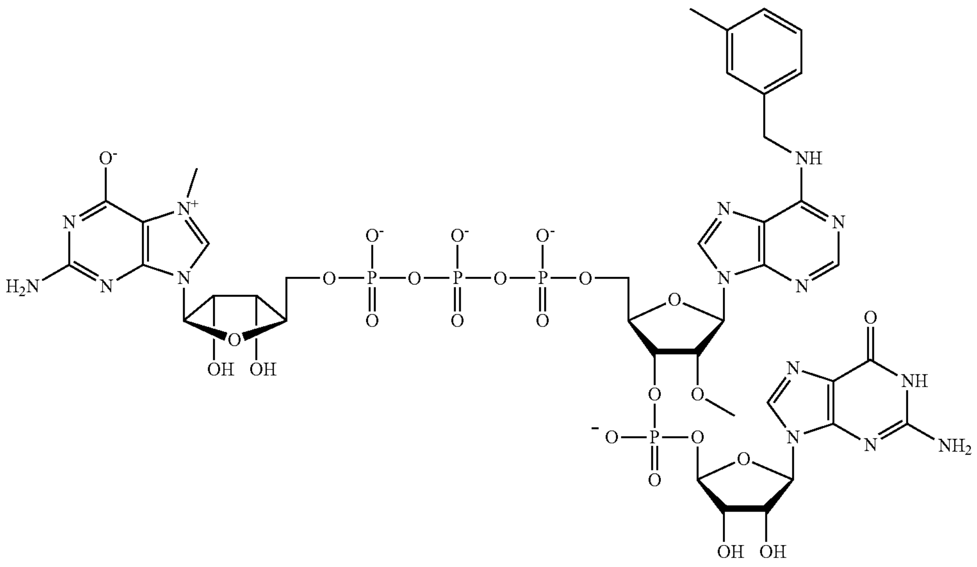
compound m$^7$Gppp$^{3Me}$Bn$^6$A$_m$pG of formula
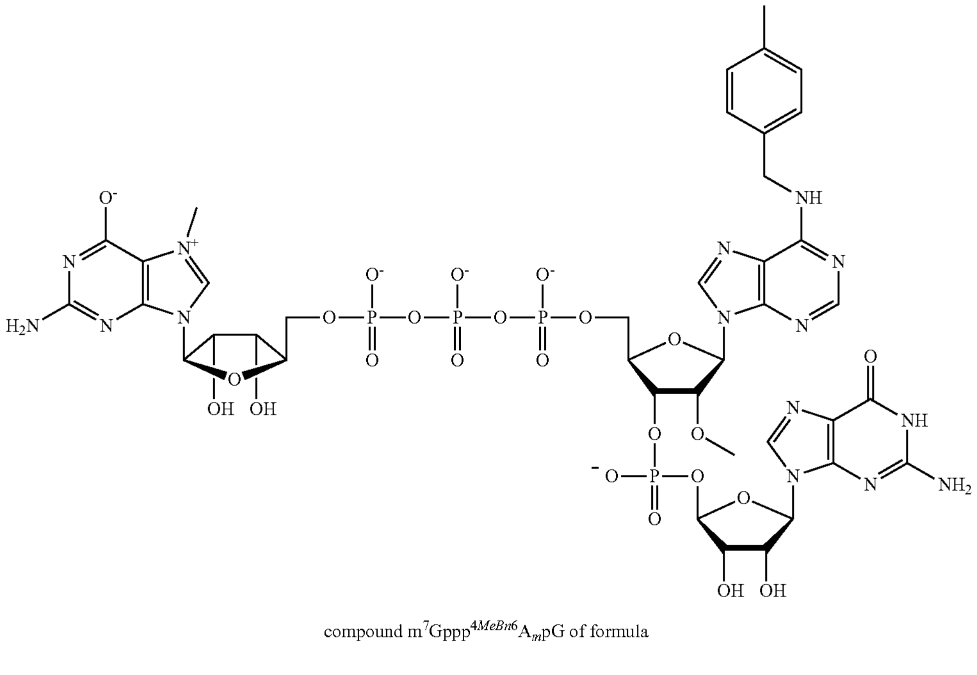
compound m$^7$Gppp$^{4MeBn6}$A$_m$pG of formula -continued
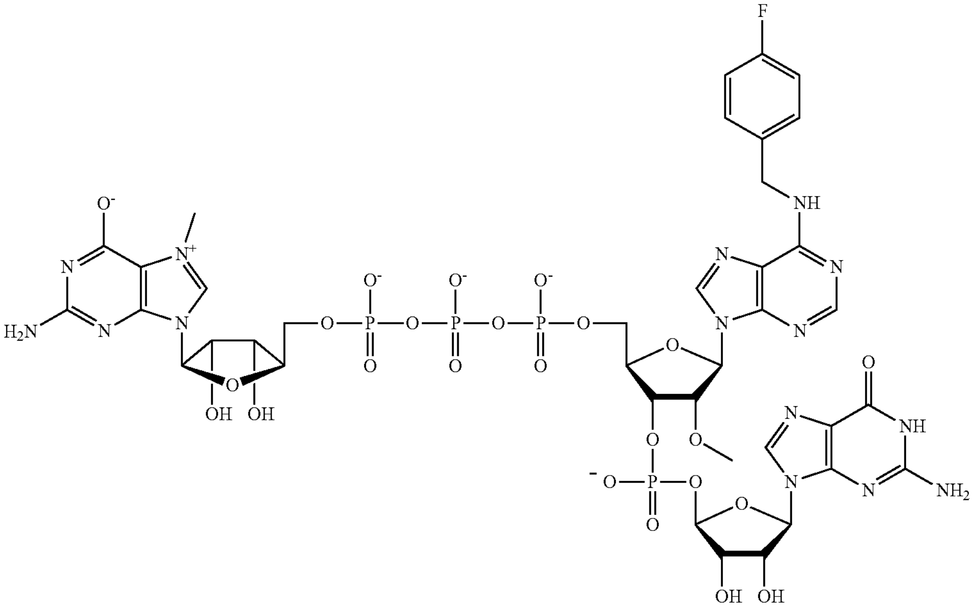
compound m$^7$Gppp$^{4FBn6}$A$_m$pG of formula
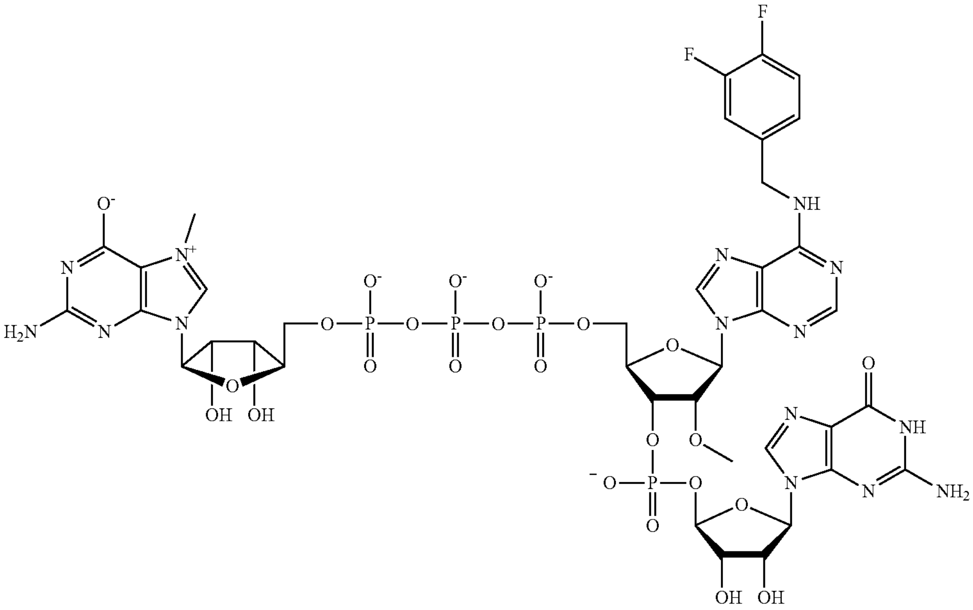
compound m$^7$Gppp$^{3,4diFBn6}$A$_m$pG of formula -continued
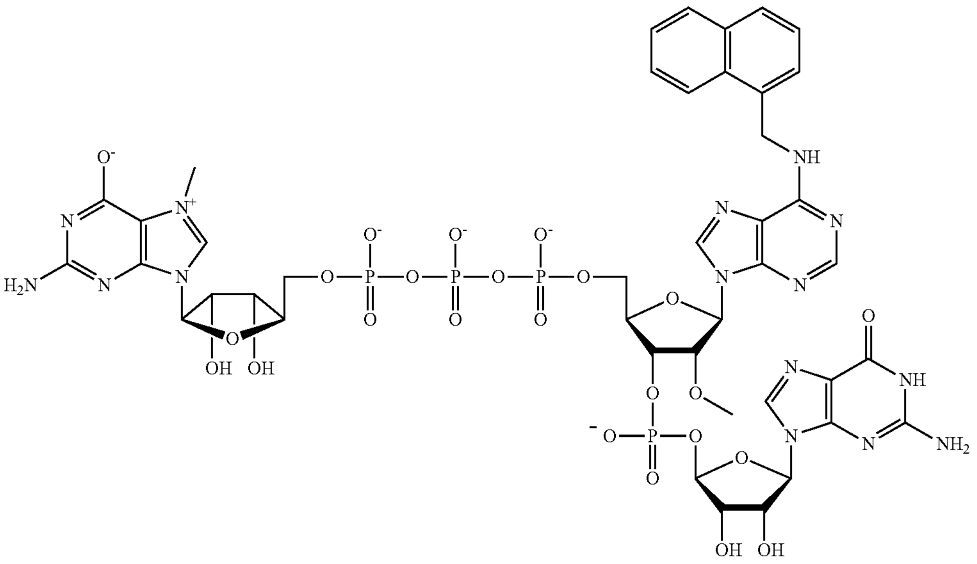
compound $m^7Gppp^{1Naphm6}A_mpG$ of formula
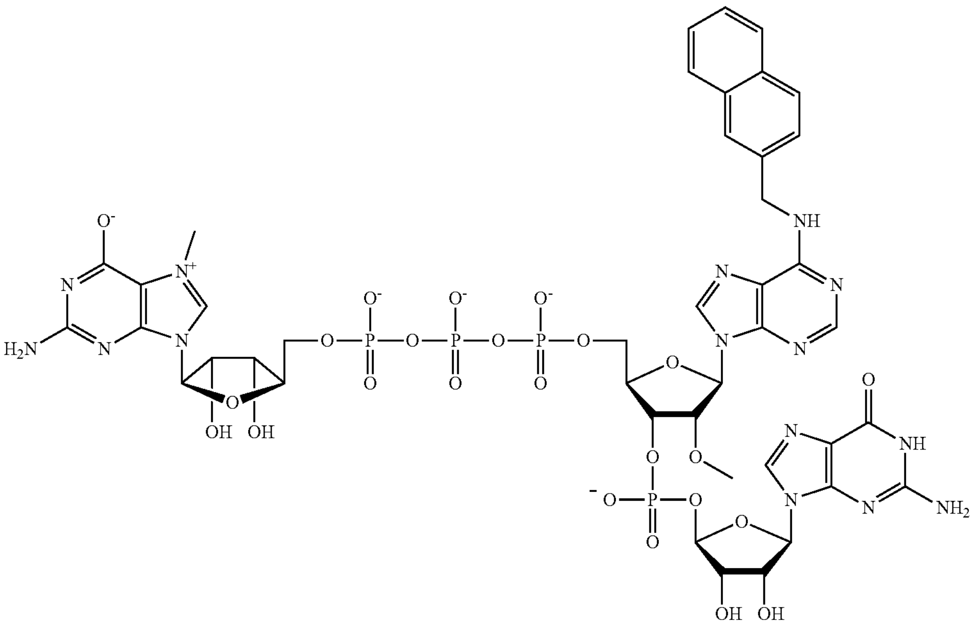
compound $m^7Gppp^{2Naphm6}A_mpG$ of formula -continued
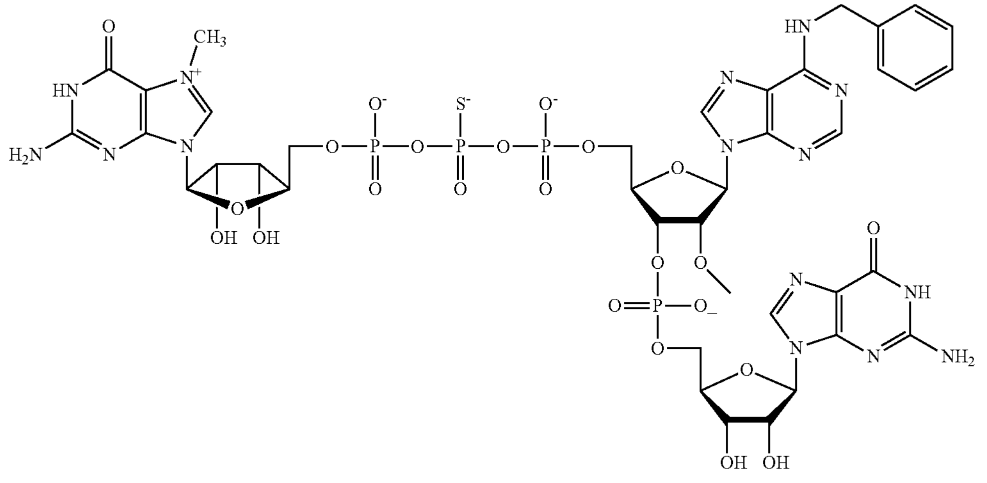
compound m$^{7}$Gpp$_{s}$p$^{Bn6}$A$_{m}$pG of formula
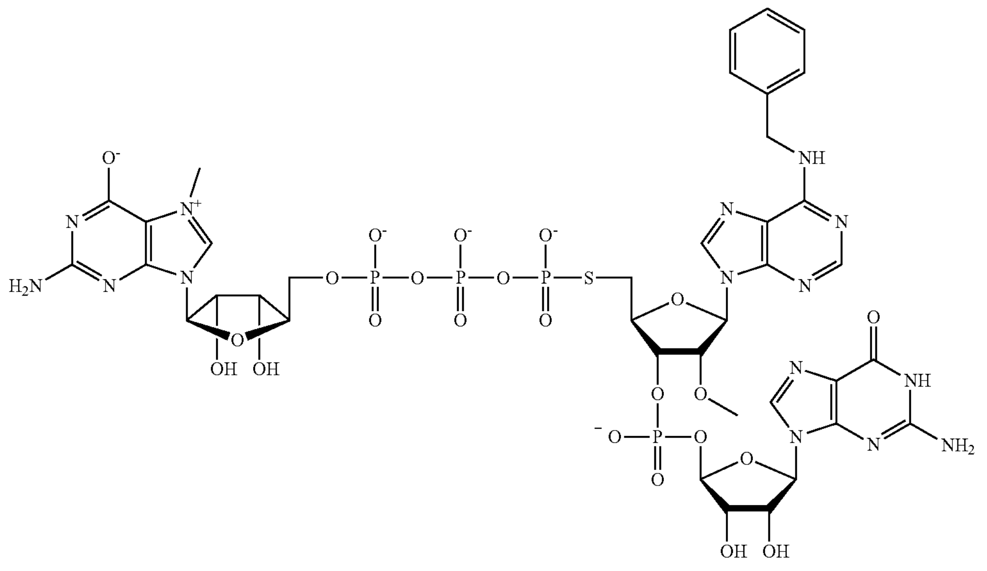
compound m$^{7}$Gppp$^{5'S,Bn6}$A$_{m}$pG of formula -continued

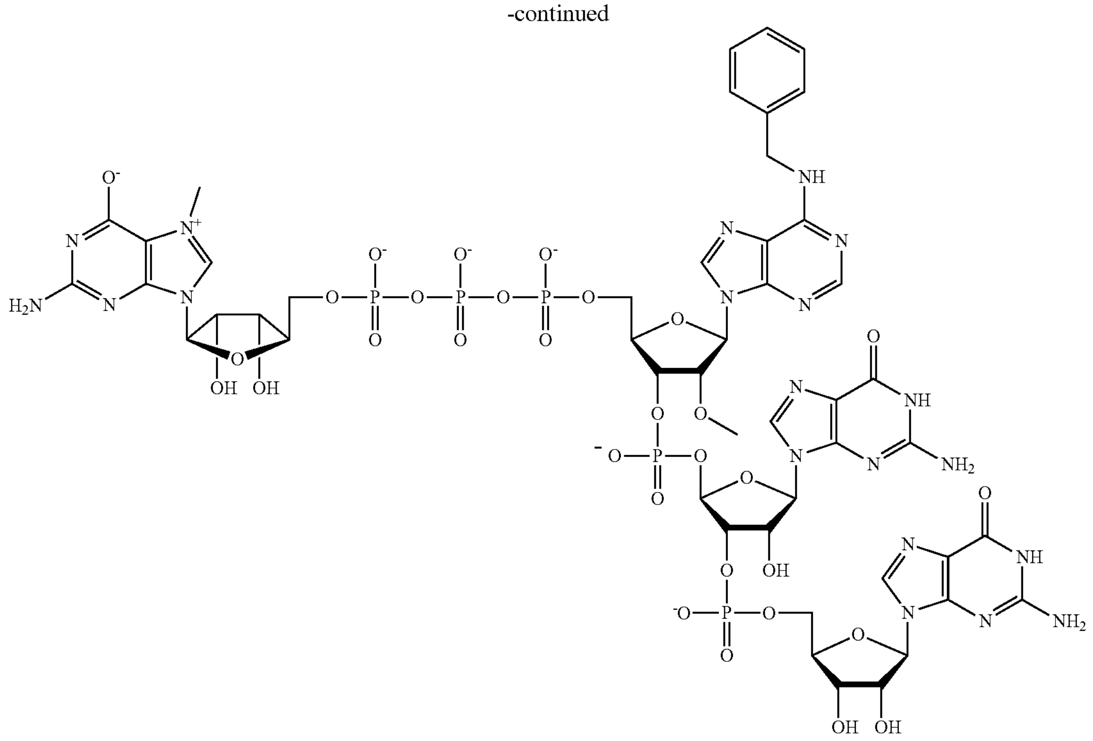

compound $m^7Gppp^{Bn6}A_mpGpG$ of formula

Preferably, the compound according to the invention consists essentially of a single stereoisomer or comprises a mixture of at least two stereoisomers, a first diastereoisomer and a second diastereoisomer, the diastereoisomers being identical except that they have different stereochemical configurations around a stereogenic phosphorus atom, said stereogenic phosphorus atom being bonded to a sulfur atom, a selenium atom, or a borane group.

Another embodiment of the invention is an RNA molecule which at the 5' end contains a compound according to the invention as defined above.

A further embodiment of the invention is a method for in vitro synthesis of an RNA molecule according to the invention as defined above, said method comprising reacting ATP, CTP, UTP and GTP, a compound according to the invention as defined above, and a polynucleotide template in the presence of an RNA polymerase, under conditions that allow the RNA polymerase to synthesize RNA copies on the polynucleotide template; whereby some of the RNA copies will contain a compound according to the invention, resulting in the production of an RNA molecule according to the invention.

Another embodiment of the invention is a method for synthesizing a protein or peptide in vitro, said method comprising translating an RNA molecule according to the invention, in a cell-free protein synthesis system, the RNA molecule comprising an open reading frame, under conditions that allow translation from the open reading frame of the RNA molecule to form a protein or peptide encoded by the open reading frame.

Another embodiment of the invention is a method for synthesizing a protein or peptide in a living cell, characterized in that it comprises incorporating an RNA molecule according to the invention into a cell, said RNA molecule comprising an open reading frame, under conditions that allow translation from the open reading frame of the RNA molecule with formation of a protein or peptide encoded by said open reading frame, said cell not being contained in a patient's body.

Another embodiment of the invention is a method for purifying an RNA molecule according to the invention characterized in that it comprises using a chromatographic method, preferably a reversed-phase HPLC method, whereby column is equilibrated, sample containing an RNA molecule according to the invention is introduced onto the chromatographic column, separation of the components of the sample in a buffered aqueous solution/organic solvent system takes place, and fractions containing the RNA molecule according to the invention are collected, whereby the RNA molecules according to the invention are separated from RNA molecules that do not contain at the 5' end compounds with structures according to the invention defined above.

Another embodiment of the invention is to use a compound according to the invention in the in-vitro synthesis of an RNA molecule.

Another embodiment of the invention is to use an RNA molecule according to the invention in the in-vitro synthesis of a protein or peptide.

Another embodiment of the invention is a compound according to the invention or an RNA molecule according to the invention for use in medicine, pharmacy or diagnostics.

It has surprisingly been found that the tri- or tetranucleotide analogues of the mRNA 5' end cap according to the invention enable easy purification of in vitro transcribed mRNA by facilitating the separation of mRNAs capped with them from uncapped mRNAs by available chromatographic methods, especially reversed-phase HPLC.

Equally surprisingly, the invention enables the production of mRNAs that have significantly higher protein expression efficiency than mRNA obtained using known mRNA 5'-end cap analogs.

Unexpectedly, these properties were obtained by introducing a hydrophobic substituent at the N6-adenosine position of the trinucleotide or tetranucleotide cap analogue. This modification results in a significant change in the migration of cap analogs and capped mRNAs on reversed-phase packed chromatography columns, allowing the separation of capped and uncapped mRNAs. Independently, this modification results in increased efficiency of mRNA expression in eukaryotic cells. Furthermore, this modification does not preclude incorporation of other previously identified cap modifications that improve mRNA properties, such as triphosphate bridge modifications or natural epigenetic modifications in the form of methylation of the 2'-O position of the first or second transcribed nucleotide, and can therefore be used together with them.

The publications cited in the description and the references given therein are hereby incorporated as references.

BRIEF DESCRIPTION OF THE FIGURES

For a better understanding of the invention, it has been illustrated in the working examples and the attached drawings, in which.

Figure 1:
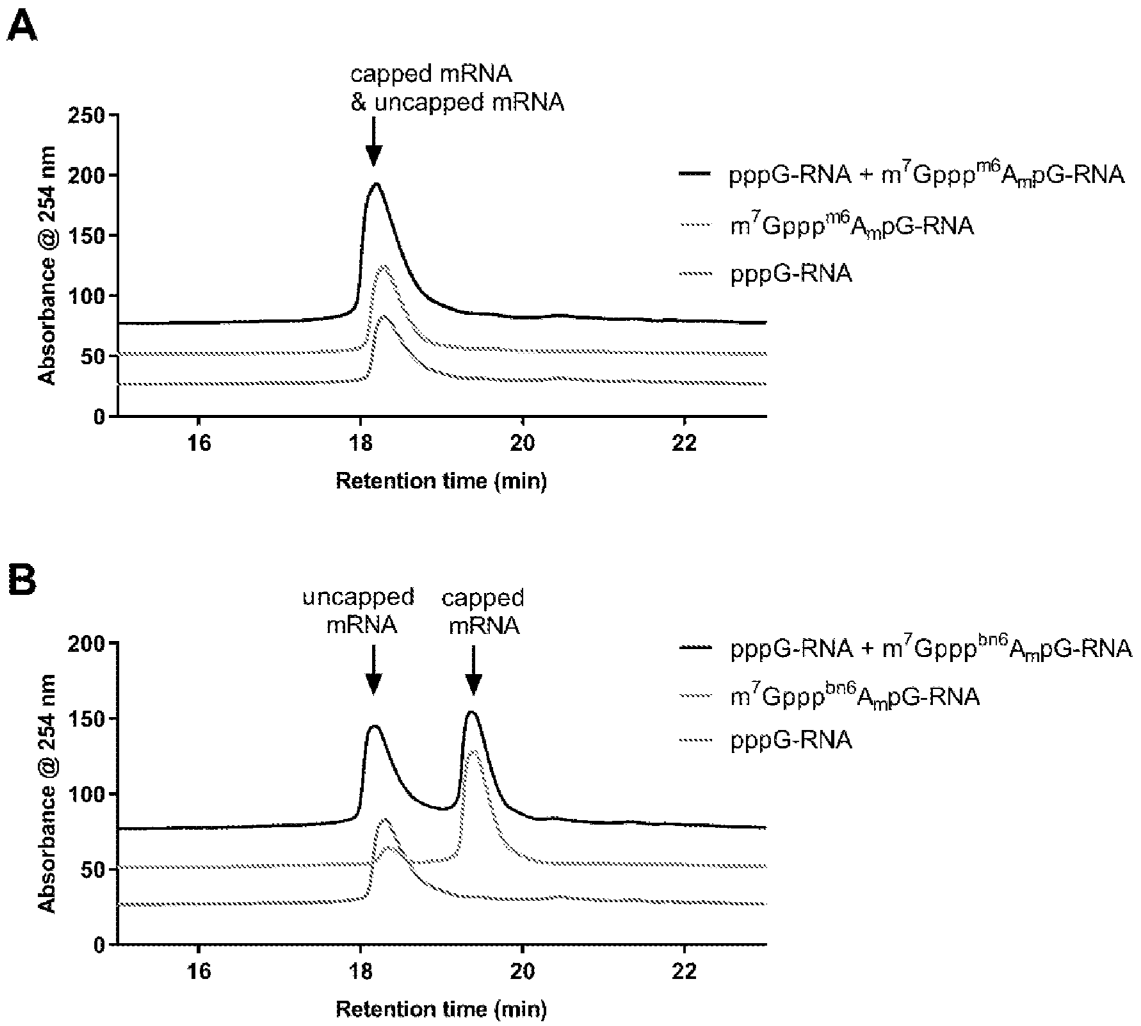
FIG. 1 depicts the reversed-phase HPLC purification of mRNA obtained using various cap analogs.

The term "alkyl" refers to a saturated, linear or branched hydrocarbon substituent with the indicated number of carbon atoms, preferably from 1 to 10 carbon atoms.

Examples of the alkyl substituent are -methyl, -ethyl, -n-propyl, -n-butyl, -n-pentyl, -n-hexyl, -n-heptyl, -n-octyl, -n-nonyl, and -n-decyl. Representative branched —(C1-C10) alkyls include -isopropyl, -sec-butyl, -isobutyl, -tert-butyl, -isopentyl, -neopentyl, -1-methylbutyl, -2-methylbutyl, -3-methylbutyl, -1, 1-dimethylpropyl, -1,2-dimethylpropyl, -1-methylpentyl, -2-methylpentyl, -3-methylpentyl, -4-methylpentyl, -1-ethylbutyl, -2-ethylbutyl, -3-ethylbutyl, -1, 1-dimethylbutyl, -1,2-dimethylbutyl, 1,3-dimethylbutyl, -2,2-dimethylbutyl, -2,3-dimethylbutyl, -3,3-dimethylbutyl, -1-methylhexyl, 2-methylhexyl, -3-methylhexyl, -4-methylhexyl, -5-methylhexyl, -1,2-dimethylpentyl, -1,3-dimethylpentyl, -1,2-dimethylhexyl, -1,3-dimethylhexyl, -3,3-dimethylhexyl, 1,2-dimethylheptyl, -1,3-dimethylheptyl, and -3,3-dimethylheptyl and the like.

The term "aryl" refers to an unsaturated, ring, aromatic or heteroaromatic (i.e. containing a heteroatom instead of carbon) hydrocarbon substituent having the indicated number of carbon atoms, preferably from 6 to 10 carbon atoms. Examples of aryl are: phenyl, naphthyl, anthracyl, phenanthryl, pyridyl.

The term "alkylaryl" refers to an unsaturated hydrocarbon substituent constructed from an alkyl and aryl portion linked together (as defined above). Examples of alkylaryl are benzyl, phenylethyl, phenylpropyl, naphthylmethyl, naphthylethyl, etc.

The term "heteroatom" means an atom selected from the group oxygen, sulfur, nitrogen, phosphorus and others.

The term "HPLC" means high performance liquid chromatography, and the solvents designated as solvents for "HPLC" mean solvents of adequate purity for HPLC (High Performance Liquid Chromatography) analysis.

The term "NMR" means Nuclear Magnetic Resonance.

WAYS OF IMPLEMENTING THE INVENTION

The following examples are provided solely to illustrate the invention and to clarify its particular aspects, and not to limit it and should not be equated with its entire scope as defined in the appended claims. In the examples below, unless otherwise indicated, standard materials and methods used in the field were used or manufacturer's recommendations for specific materials and methods were followed.

EXAMPLES

Tri- and tetranucleotide cap analogs were synthesized as described in Examples 1-6 combining solid phase synthesis and solution synthesis methods, followed by isolation using a two-step purification procedure. The starting point was the synthesis of appropriately modified oligonucleotides: dinucleotides (pA*pG, where A* stands for adenosine substituted at the N6 position) or trinucleotides (pA*pGpG) on a highly loaded support using the phosphoramidite method, as described in Example 2.[11] The corresponding phosphoramidites modified at the N6-position of adenosine were obtained by N-alkylation of commercially available adenosine phosphoramidite under phase transfer catalysis conditions, as described in Example 1. Oligonucleotides were cleaved from the support, deprotected and isolated by ion exchange chromatography as triethylammonium salts suitable for activation into P-imidazolides and subsequent coupling reaction in the presence of $ZnCl_2$. Activated oligonucleotides were subjected to a coupling reaction with $m^7$GDP [12] to obtain m7GpppA*$(pG)_k$ analogues, wherein A* denotes the N6-modified adenosine, and k equals 1 or 2, as described in Examples 3 and 6.

Example 3 shows examples of preparation of trinucleotide cap analogs modified at N6 position of adenosine with groups such as benzyl, substituted benzyl, 1-naphthylmethyl, 2-naphthylmethyl. Other trinucleotides, unmodified within the triphosphate bridge according to claim 1, can be synthesized using a procedure analogous to that described in Example 3, using pA*pG dinucleotides (appropriately modified at N6 position of adenosine), obtained as described in Example 2. Examples 4 and 5 show examples of preparation of trinucleotide cap analogs modified at N6 position of adenosine with benzyl moiety and additionally containing modification within 5',5'-triphosphate bridge. The synthesis of β-thiophosphate (β-phosphorothioate) analogues (Example 4) required the transformation of $p^{Bn6}$$A_m$pG into the corresponding P-imidazolide, which was then coupled with $m^7$GDP-β-S [12]. The compounds were isolated by ion exchange chromatography and further purified by RP HPLC to give ammonium salts suitable for biological studies. In the case of β-phosphorothioates, the product was obtained as a mixture of two stereoisomers that could not be separated at the RP HPLC purification stage, so they were isolated as a mixture. the synthesis of 5'-phosphorothiolate cap analog (Example 5), required a 2-step modification of 5'-deprotected oligonucleotide on solid support, in order to incorporate sulfur atom at the 5' position of adenosine. Other tri- or tetranucleotides modified within triphosphate bridge can be synthesized using strategies described in Examples 1-6, using appropriate N6-modified adenosine phosphoramidites and appropriate N6-modfiied oligonucleotides (pA*pG or pA*pGpG), combined with methods of triphosphate bridge modifications described in the literature for dinucleotide cap analogs.[17, 18, 19, 20, 21]

Example 6 shows an example of preparation of tetranucleotide cap analog, modified at N6 of adenosine position with benzyl group. Other tetranucleotides, unmodified within the triphosphate bridge according to claim 1, can be synthesized using a procedure analogous to that described in Example 6, using pA*pGpG trinucleotides appropriately modified at N6 position of adenosine.

Figure 2:
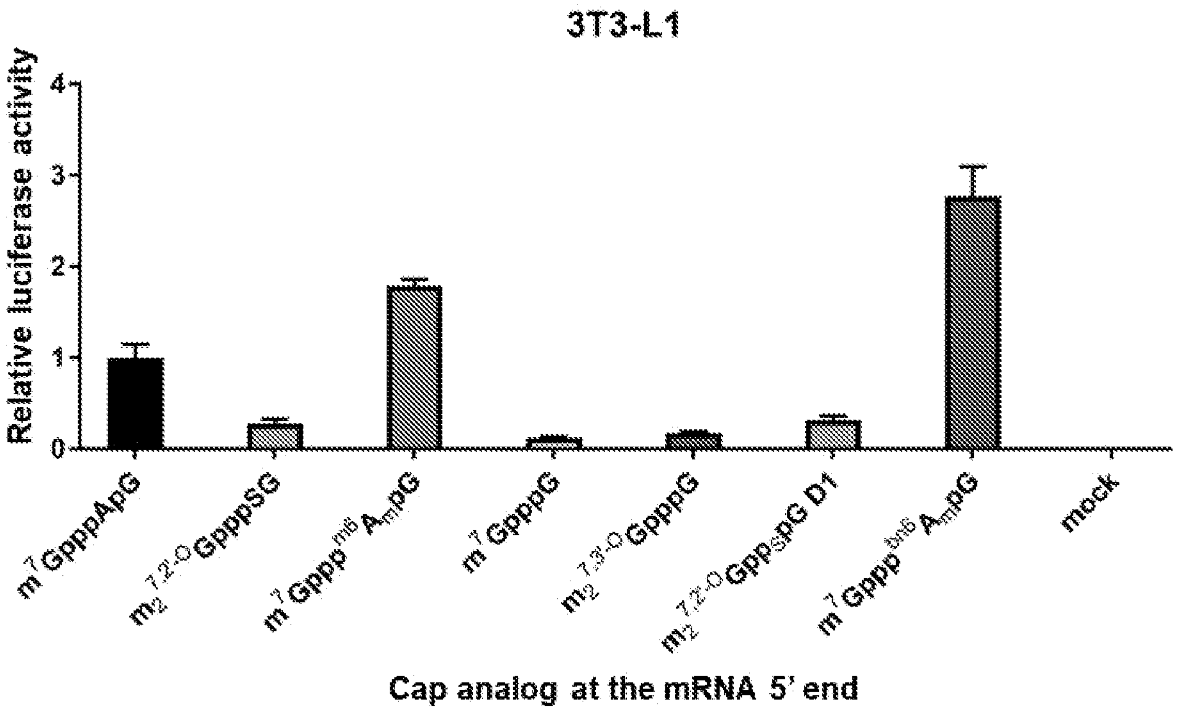
FIG. 2 shows protein expression in 3T3-L1 cells from HPLC-purified mRNA.
Figure 3:
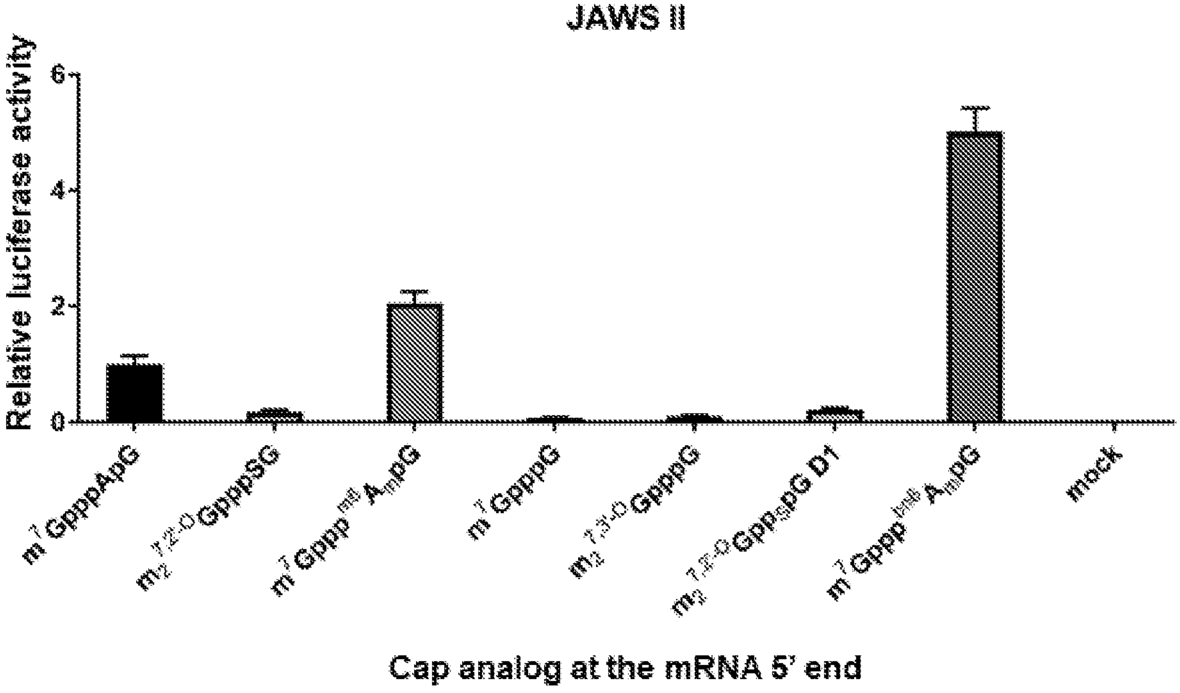
FIG. 3 shows protein expression in JAWSII cells obtained from mRNAs capped with selected analogs ($m^7$GpppApG, $m_2^{7,2'O}$-GpppSG, $m^7$Gppp$^{m6}$$A_m$pG, $m^7$GpppG, $m_2^{7,2'-O}$ GpppG, $m_2^{7,2'-O}$ Gpp$_S$pG D1, $m^7$Gppp$^{Bn6}$$A_m$pG) purified by HPLC.
Figure 4:
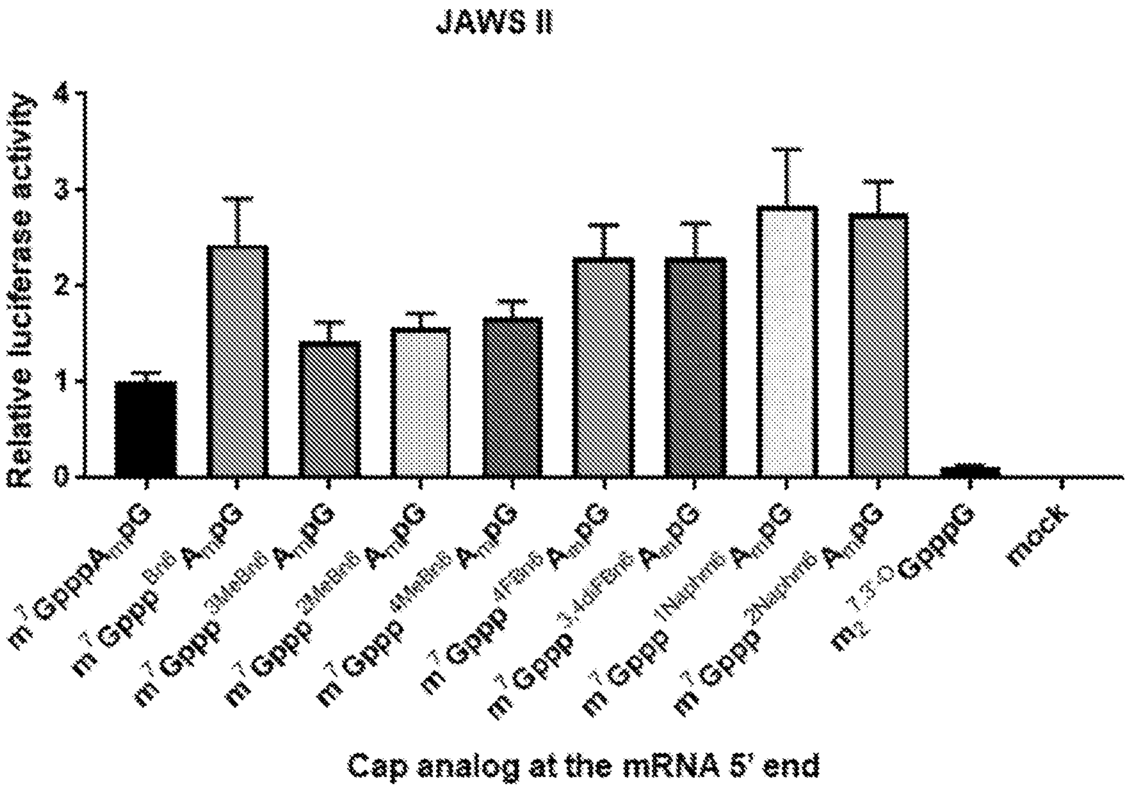
FIG. 4 shows protein expression in JAWSII cells obtained from mRNAs capped with selected analogs ($m^7$Gppp$A_m$pG, $m^7$Gppp$^{Bn6}$$A_m$pG, $m^7$Gppp$^{3MeBn6}$$A_m$pG, $m^7$Gppp$^{2MeBn6}$$A_m$pG, $m^7$Gppp$^{4MeBn6}$$A_m$pG, $m^7$Gppp$^{4FBn6}$$A_m$pG, $m^7$Gppp$^{3,4diFBn6}$$A_m$pG, $m^7$Gppp$^{1Naphm6}$$A_m$pG, $m^7$Gppp$^{2Naphm6}$$A_m$pG, $m_2^{7,2'-O}$ GpppG) purified by HPLC.

Transcripts incorporating at the 5' end the compounds according to the invention or benchmark (reference) compounds were obtained by in vitro transcription in the presence of T7 RNA polymerase and DNA template containing the ϕ6.5 promoter sequence for this polymerase. To analyze the protein expression efficiency in mammalian cells, mRNA transcripts containing compounds of the invention or reference compounds and encoding *Gaussia* luciferase as a reporter gene were obtained. The in vitro transcription reaction was carried out under the conditions described in Example 7. The obtained mRNAs were pre-purified and analyzed by reversed-phase HPLC under the conditions described in Example 8. The results of this analysis juxtaposed with the results of analogous analysis for mRNA obtained using the most structurally similar unmodified trinucleotide cap analog [11](m7Gppp$^{m6}$A$_m$pG) are shown in FIG. 1. Prior to testing for protein expression efficiency, mRNAs capped with trinucleotide cap analogs of the invention were subjected to RP HPLC purification to remove double-stranded RNA impurities as described in Example 8. In each case, an increase in the retention time of the mRNA was observed compared to the non-capped mRNA or reference mRNAs (capped with m$^7$GpppApG, m$^7$GpppA$_m$pG or m$^7$Gppp$^{m6}$A$_m$pG), with the retention time of a given mRNA increasing with increasing hydrophobicity of the substituent at the N6-adenosine position (Table 1). Reference mRNAs were also subjected to HPLC purification as described in Example 8, but they were beforehand subjected to a procedure for the enzymatic removal of uncapped (5'-triphosphate) mRNA as described in Example 7. The resulting mRNA capped with compounds of the invention or reference compounds were introduced into mammalian cell lines (fibroblasts—3T3-L1 and denitric cells—JAWS II) by transfection using lipofectamine, followed by measuring the level of *Gaussia* luciferase expression in the extracellular medium at appropriate intervals as described in Example 9. The results of these experiments are shown in FIG. 2, FIG. 3 and FIG. 4, which show the overall (total) expression level of *Gaussia* luciferase obtained throughout the experiment (88 h), being the sum of *Gaussia* luciferase expression levels obtained at individual time points.

Example 1: Synthesis of N$^6$-modified 2'-O-methyladenosine 3'-O-phosphoramidites (A*-CEP)

3'-O-phosphoramidite of 5'-O-dimethoxytrityl-N6-phenoxyacetyl-2'-O-methyladenosine (5'-O-DMT-2'-O-Me-rA$^{Pac}$) (1 equivalent) and benzyl bromide (4 equivalents) were dissolved in $CH_2Cl_2$ (to get 0.1 M solution of phosphoramidite) and mixed with an solution of tetrabutylammonium bromide (1 equivalent) in 1 M NaOH (1 volume of the reaction mixture). The mixture was stirred vigorously for 30 min and then diluted with 50 mL of water and 50 mL of diethyl ether. The layers were separated and the aqueous phase was extracted twice with diethyl ether (50 mL). Organic layers were combined, dried over anhydrous $Na_2SO_4$ and evaporated. The residue was dissolved in $CH_2Cl_2$ with triethylamine (0.5% v/v) and evaporated with silica-gel. The product was isolated by flash chromatography on 20 g silica-gel column using gradient elution (0→100% ethyl acetate in n-hexane) to afford after evaporation a mixture of diastereomers of A*-CEP phosphoramidite as a white foam.

| Compound (A*-CEP) | Chemical structure | Synthesis scale [μmol] | Yield [μmol] |
|---|---|---|---|
| $^{Bn6}$A$_m$-CEP | 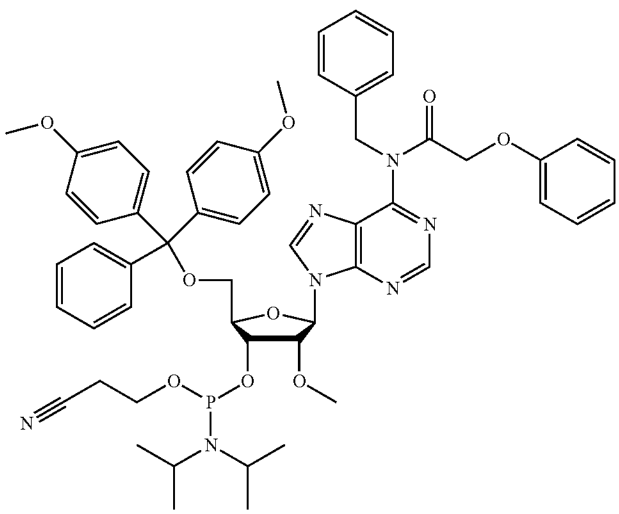 | 1089 | 640 |

-continued
| Compound (A*-CEP) | Chemical structure | Synthesis scale [μmol] | Yield [μmol] |
|---|---|---|---|
| $^{2MeBn6}A_m$-CEP | 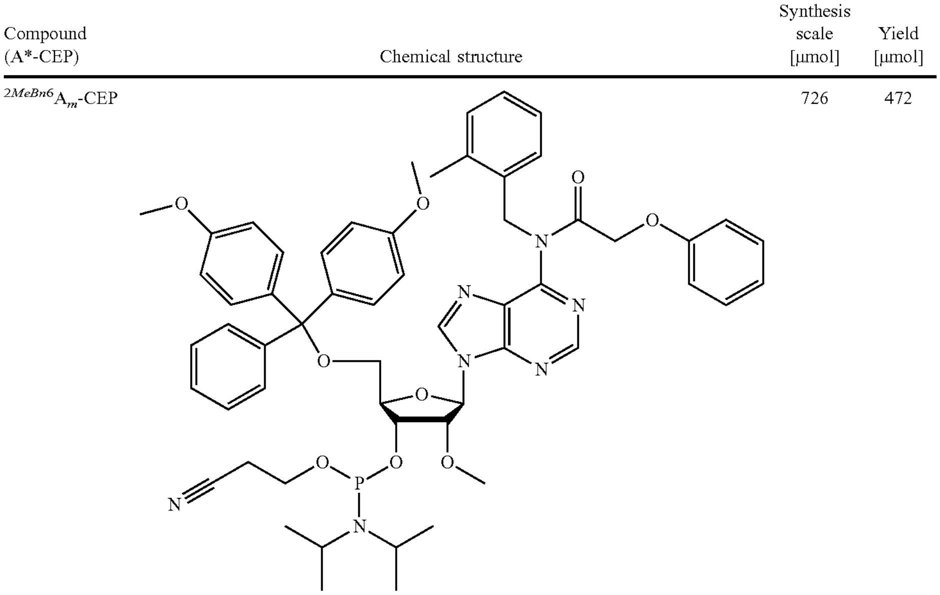 | 726 | 472 |
| $^{3MeBn6}$Am-CEP | 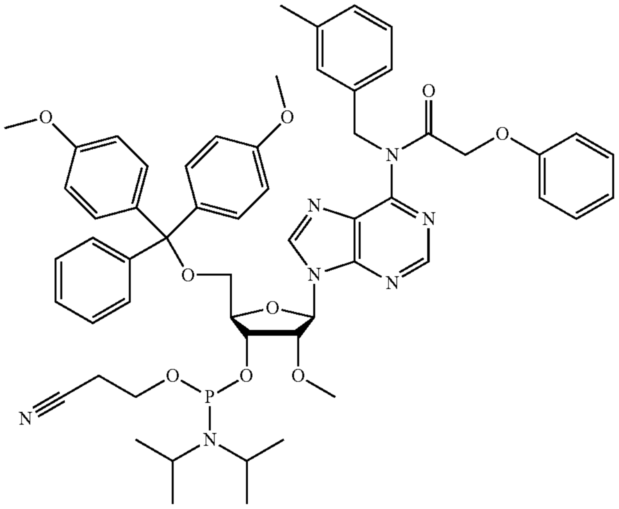 | 564 | 360 |
| $^{4MeBn6}$Am-CEP | 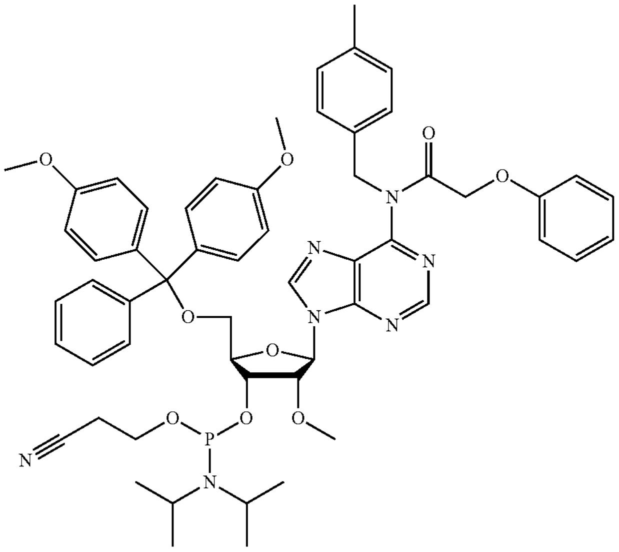 | 726 | 545 |

-continued
| Compound (A*-CEP) | Chemical structure | Synthesis scale [μmol] | Yield [μmol] |
|---|---|---|---|
| $^{4FBn6}$Am-CEP | 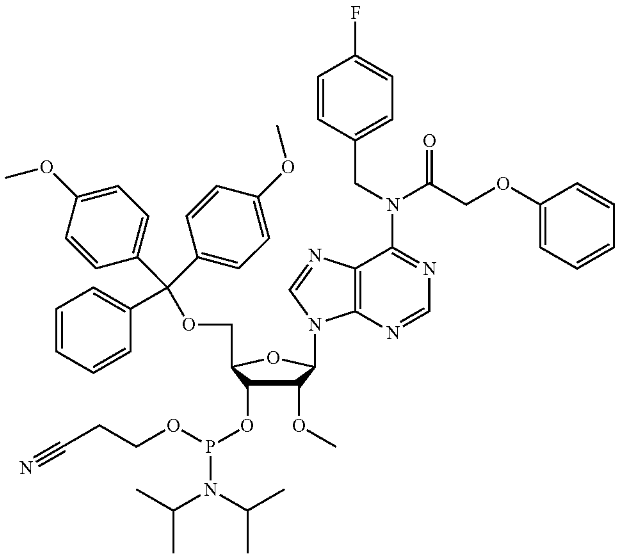 | 363 | 249 |
| $^{3,4diFBn6}$Am-CEP | 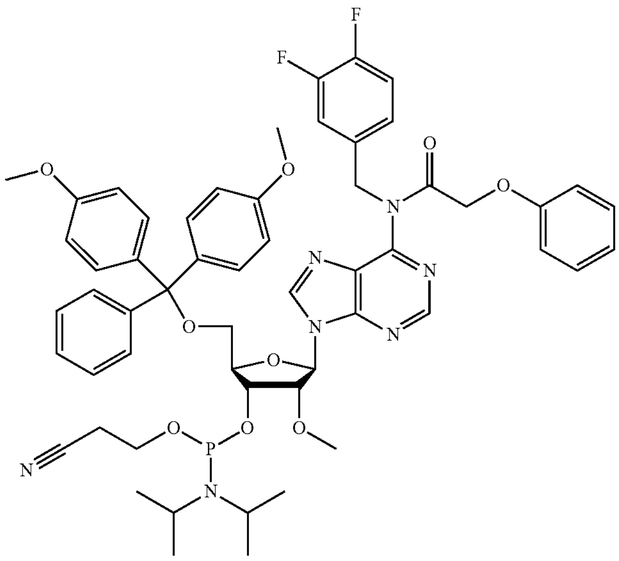 | 363 | 248 |

-continued

| Compound (A*-CEP) | Chemical structure | Synthesis scale [μmol] | Yield [μmol] |
|---|---|---|---|
| $^{1Naphm6}$Am-CEP | 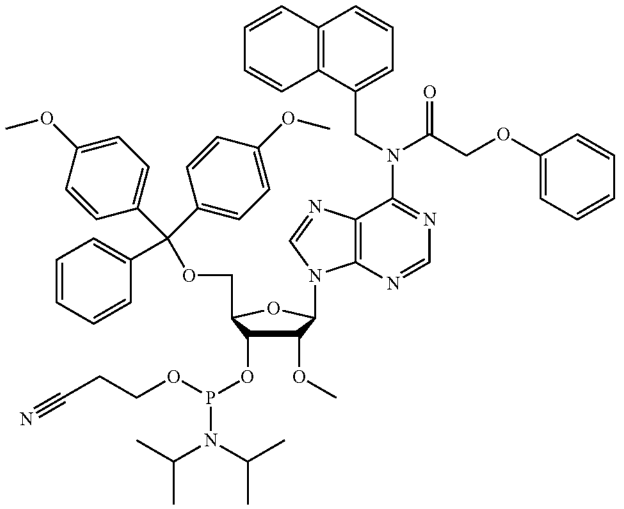 | 363 | 246 |
| $^{2Naphm6}$Am-CEP | 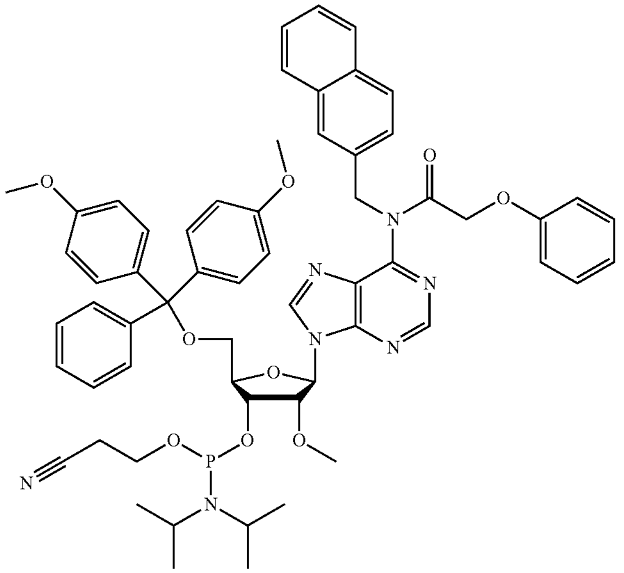 | 363 | 280 |

$^{Bn6}A_m$-CEP: $^1$H NMR (500 MHz, $CDCl_3$, 25° C.): δ=8.60 (s, 1H, H8), 8.58 (s, 1H, H8), 8.26 (s, 1H, H2), 8.19 (s, 1H, H2), 7.46-6.60 (m, 46H, ArH), 6.15 (d, $^3J_{H,H}$=5.4 Hz, 1H, H1'), 6.13 (d, $^3J_{H,H}$=5.0 Hz, 1H, H1'), 5.65 (s, 4H, $CH_{2(bn6)}$) 5.13 (s, 4H, $CH_2$(Pac)), 4.67 (m, 2H, H3'), 4.54 (m, 2H, H2'), 4.41 (m, 1H, H4'), 4.35 (m, 1H, H4'), 3.90 (m, 2H, $OCH_2CH_2CN$), 3.77 (s, 12H, $OCH_{3\ DMT}$), 3.72-3.52 (m, 8H, $OCH_2CH_2CN$, H5', $CH_{iPr}$), 3.48 (s, 6H, $CH_{3,\ 2'-O}$), 3.38 (dd, $^2J_{H,H}$=10.6 Hz, $^3J_{H,H}$=3.8 Hz, 2H, H5"), 2.63 (t, $^3J_{H,H}$=6.3 Hz, 2H, $OCH_2CH_2CN$), 2.37 (t, $^3J_{H,H}$=6.3 Hz, 2H, $OCH_2CH_2CN$), 1.19 (m, 24H, $CH_{3\ iPr}$) ppm; $^{31}$P NMR (202.5 MHz, $CDCl_3$, $H_3PO_4$, 25° C.): δ=151.0 (s, 1P, P), 150.3 (s, 1P, P) ppm;

$^{2MeBn6}A_m$-CEP: $^1$H NMR (500 MHz, $CDCl_3$, TMS, 25° C.): δ=8.62 (s, 1H, H8), 8.60 (s, 1H, H8), 8.24 (s, 1H, H2), 8.17 (s, 1H, H2), 7.45-6.62 (m, 44H, ArH), 6.13 (d, $^3J_{H,H}$=4.8 Hz, 1H, H1'), 6.11 (d, $^3J_{H,H}$=5.0 Hz, 1H, H1'), 5.63 (s, 4H, $CH_{2\ (2MeBn)}$) 5.15 (s, 4H, $CH_{2\ (Pac)}$), 4.65 (m, 1H, H3'), 4.57 (m, 2H, H3', H2'), 4.50 (m, 1H, H2'), 4.40 (m, 1H, H4'), 4.34 (m, 1H, H4'), 3.88 (m, 2H, $OCH_2CH_2CN$), 3.77 (4×s, 12H, $OCH_{3\ (DMTr)}$), 3.71-3.50 (m, 8H, $OCH_2CH_2CN$, H5', $CH_{(iPr)}$), 3.46 (6H, $CH_{3\ (2'-O)}$), 3.36 (m, 2H, H5"), 2.62 (t, $^3J_{H,H}$=6.3 Hz, 2H, $OCH_2CH_2CN$), 2.37 (t, $^3J_{H,H}$=6.4 Hz, 2H, $OCH_2CH_2CN$), 2.33 (s, 6H, $CH_{3\ (2MeBn)}$) 1.19 (m, 18H, $CH_{3(iPr)}$), 1.07 (d, $^3J_{H,H}$=6.8 Hz, 6H, $CH_{3(iPr)}$) ppm; $^{31}$P NMR (202.5 MHz, $CDCl_3$, $H_3PO_4$, 25° C.): δ=151.0 (s, 1P, P), 150.4 (s, 1P, P) ppm;

$^{3MeBn6}A_m$-CEP: $^1$H NMR (500 MHz, $CDCl_3$, TMS, 25° C.): δ=8.60 (s, 1H, H8), 8.59 (s, 1H, H8), 8.26 (s, 1H, H2), 8.20 (s, 1H, H2), 7.46-6.61 (m, 44H, ArH), 6.15 (d, $^3J_{H,H}$=5.2 Hz, 1H, H1'), 6.14 (d, $^3J_{H,H}$=5.1 Hz, 1H, H1'), 5.62 (s, 4H, $CH_{2\ (3MeBn)}$) 5.14 (s, 4H, $CH_{2\ (Pac)}$), 4.66 (m, 1H, H3'), 4.60 (m, 1H, H3'), 4.58 (m, 1H, H2'), 4.54 (m, 1H, H2'), 4.41 (m, 1H, H4'), 4.36 (m, 1H, H4'), 3.89 (m, 2H, $OCH_2CH_2CN$), 3.77 (4×s, 12H, $OCH_{3(DMTr)}$), 3.73-3.50 (m, 8H, $OCH_2H_2OCN$, H5', $CH_{(iPr)}$), 3.48 (2×s, 6H, $CH_{3\ (2'-O)}$), 3.37 (m, 2H, H5"), 2.63 (t, $^3J_{H,H}$=6.3 Hz, 2H, $OCH_2CH_2CN$), 2.37 (t, $^3J_{H,H}$=6.3 Hz, 2H, $OCH_2CH_2CN$), 2.23 (s, 6H, $CH_{3\ (3MeBn)}$) 1.20 (m, 18H, $CH_{3(iPr)}$), 1.08 (d, $^3J_{H,H}$=6.8 Hz, 6H, $CH_{3\ (iPr)}$) ppm; $^{31}$P NMR (202.5 MHz, $CDCl_3$, $H_3PO_4$, 25° C.): δ=151.1 (s, 1P, P), 150.4 (s, 1P, P) ppm;

$^{4MeBn6}A_m$-CEP: $^1$H NMR (500 MHz, $CDCl_3$, TMS, 25° C.): δ=8.59 (s, 1H, H8), 8.57 (s, 1H, H8), 8.26 (s, 1H, H2), 8.19 (s, 1H, H2), 7.45-6.61 (m, 44H, ArH), 6.15 (d, $^3J_{H,H}$=5.1 Hz, 1H, H1'), 6.13 (d, $^3J_{H,H}$=5.0 Hz, 1H, H1'), 5.61 (s, 4H, $CH_{2\ (4MeBn)}$) 5.12 (s, 4H, $CH_{2\ (Pac)}$), 4.67 (m, 1H, H3'), 4.60 (m, 1H, H3'), 4.58 (m, 1H, H2'), 4.54 (m, 1H, H2'), 4.41 (m, 1H, H4'), 4.36 (m, 1H, H4'), 3.89 (m, 2H, $OCH_2CH_2CN$), 3.77 (4×S, 12H, $OCH_{3\ (DMTr)}$), 3.73-3.50 (m, 8H, $OCH_2CH_2CN$, H5', $CH_{(iPr)}$), 3.48 (6H, $CH_{3\ (2'-O)}$), 3.36 (m, 2H, H5"), 2.63 (t, $^3J_{H,H}$=6.3 Hz, 2H, $OCH_2CH_2CN$), 2.37 (t, $^3J_{H,H}$=6.3 Hz, 2H, $OCH_2CH_2CN$), 2.22 (s, 6H, $CH_{3(4MeBn)}$) 1.20 (m, 18H, $CH_{3\ (iPr)}$), 1.08 (d, $^3J_{H,H}$=6.8 Hz, 6H, $CH_{3\ (iPr)}$) ppm; $^{31}$P NMR (202.5 MHz, $CDCl_3$, $H_3PO_4$, 25° C.): δ=151.0 (s, 1P, P), 150.4 (s, 1P, P) ppm;

$^{1Naph6}A_m$-CEP: $^1$H NMR (500 MHz, $CDCl_3$, TMS, 25° C.): δ=8.59 (s, 1H, H8), 8.58 (s, 1H, H8), 8.24 (s, 1H, H2), 8.16 (s, 1H, H2), 8.14 (d, $^3J_{H,H}$=8.4 Hz, 2H, $ArH_{Naph}$), 7.78 (d, $^3J_{H,H}$=8.1 Hz, 2H, $ArH_{Naph}$), 7.63 (d, $^3J_{H,H}$=8.2 Hz, 2H, $ArH_{Naph}$), 7.51 (m, 2H, $ArH_{Naph}$), 7.45 (m, 2H, $ArH_{Naph}$), 7.43-6.63 (m, 40H, ArH), 6.13 (s, 4H, $CH_{2\ (1NaphCH2)}$), 6.11 (d, $^3J_{H,H}$=4.9 Hz, 1H, H1'), 6.10 (d, $^3J_{H,H}$=5.0 Hz, 1H, H1'), 5.17 (s, 4H, $CH_{2\ (Pac)}$), 4.63 (m, 1H, H3'), 4.56 (m, 2H, H3', H2'), 4.48 (m, 1H, H2'), 4.38 (m, 1H, H4'), 4.33 (m, 1H, H4'), 3.87 (m, 2H, $OCH_2CH_2CN$), 3.75 (4×s, 12H, $OCH_{3\ (DMTr)}$), 3.70-3.53 (m, 8H, $OCH_2CH_2CN$, H5', $CH_{(iPr)}$), 3.44 (6H, $CH_{3\ (2'-O)}$), 3.34 (m, 2H, H5"), 2.60 (t, $^3J_{H,H}$=6.3 Hz, 2H, $OCH_2CH_2CN$), 2.34 (t, $^3J_{H,H}$=6.3 Hz, 2H, $OCH_2CH_2CN$), 1.17 (d, $^3J_{H,H}$=6.7 Hz, 18H, $CH_3$ (iPr)), 1.06 (d, $^3J_{H,H}$=6.7 Hz, 6H, $CH_{3(iPr)}$) ppm; $^{31}$P NMR (202.5 MHz, $CDCl_3$, $H_3PO_4$, 25° C.): 6=151.0 (s, 1P, P), 150.4 (s, 1P, P) ppm;

$^{2Naph6}A_m$-CEP: $^1$H NMR (500 MHz, $CDCl_3$, TMS, 25° C.): δ=8.52 (s, 1H, H8), 8.51 (s, 1H, H8), 8.21 (s, 1H, H2), 8.14 (s, 1H, H2), 7.66 (m, 4H, $ArH_{Naph}$), 7.60 (m, 4H, $ArH_{Naph}$), 7.39-6.55 (m, 42H, ArH), 6.07 (d, $^3J_{H,H}$=4.8 Hz, 1H, H1'), 6.05 (d, $^3J_{H,H}$=4.8 Hz, 1H, H1'), 5.74 (s, 4H, $CH_{2\ (1NaphCH2)}$), 5.09 (s, 4H, $CH_{2\ (Pac)}$), 4.58 (m, 1H, H3'), 4.50 (m, 2H, H3', H2'), 4.44 (m, 1H, H2'), 4.32 (m, 1H, H4'), 4.27 (m, 1H, H4'), 3.79 (m, 2H, $OCH_2CH_2CN$), 3.69 (4×s, 12H, $OCH_{3\ (DMTr)}$), 3.64-3.44 (m, 8H, $OCH_2CH_2CN$, H5', $CH_{(iPr)}$), 3.38 (6H, $CH_{3\ (2'-O)}$), 3.28 (m, 2H, H5"), 2.53 (t, $^3J_{H,H}$=6.3 Hz, 2H, $OCH_2CH_2CN$), 2.28 (t, $^3J_{H,H}$=6.3 Hz, 2H, $OCH_2CH_2CN$), 1.10 (m, 18H, $CH_{3\ (iPr)}$), 0.99 (d, $^3J_{H,H}$=6.8 Hz, 6H, $CH_{3\ (iPr)}$) ppm; $^{31}$P NMR (202.5 MHz, $D_2O$, $H_3PO_4$, 25° C.): δ=151.0 (s, 1P, P), 150.4 (s, 1P, P) ppm;

$^{4FBn6}A_m$-CEP: $^1$H NMR (500 MHz, $CDCl_3$, TMS, 25° C.): δ=8.61 (s, 1H, H8), 8.59 (s, 1H, H8), 8.28 (s, 1H, H2), 8.21 (s, 1H, H2), 7.45-6.59 (m, 43H, ArH), 6.16 (d, $^3J_{H,H}$=4.7 Hz, 1H, H1'), 6.15 (d, $^3J_{H,H}$=4.9 Hz, 1H, H1'), 5.57 (s, 4H, $CH_{2\ (4FBn)}$) 5.12 (s, 4H, $CH_{2\ (Pac)}$), 4.69 (m, 1H, H3'), 4.64-4.60 (m, 2H, H3', H2'), 4.55 (m, 1H, H2'), 4.41 (m, 1H, H4'), 4.36 (m, 1H, H4'), 3.89 (m, 2H, $OCH_2CH_2CN$), 3.77 (4×s, 12H, $OCH_{3(DMTr)}$), 3.73-3.51 (m, 8H, $OCH_2CH_2CN$, H5', $CH_{(iPr)}$), 3.48 (6H, $CH_{3\ (2'-O)}$), 3.36 (m, 2H, H5"), 2.63 (t, $^3J_{H,H}$=6.3 Hz, 2H, $OCH_2CH_2CN$), 2.38 (t, $^3J_{H,H}$=6.3 Hz, 2H, $OCH_2CH_2CN$), 1.20 (m, 18H, $CH_{3\ (iPr)}$), 1.08 (d, $^3J_{H,H}$=6.8 Hz, 6H, $CH_{3\ (iPr)}$) ppm; $^{19}$F NMR (470.6 MHz, $D_2O$, NaF, 25° C.): δ=−115.4 (m, 1F, F) ppm; $^{31}$P NMR (202.5 MHz, $CDCl_3$, $H_3PO_4$, 25° C.): δ=151.0 (s, 1P, P), 150.4 (s, 1P, P) ppm;

$^{3,4diFBn6}A_m$-CEP: $^1$H NMR (500 MHz, $CDCl_3$, TMS, 25° C.): δ=8.62 (s, 1H, H8), 8.61 (s, 1H, H8), 8.30 (s, 1H, H2), 8.23 (s, 1H, H2), 7.46-6.58 (m, 42H, ArH), 6.17 (d, $^3J_{H,H}$=4.9 Hz, 1H, H1'), 6.16 (d, $^3J_{H,H}$=4.7 Hz, 1H, H1'), 5.53 (s, 4H, $CH_{2\ (3,4diFBn)}$) 5.13 (s, 4H, $CH_{2\ (Pac)}$), 4.70 (m, 1H, H3'), 4.65-4.58 (m, 2H, H3', H2'), 4.54 (m, 1H, H2'), 4.41 (m, 1H, H4'), 4.36 (m, 1H, H4'), 3.88 (m, 2H, $OCH_2CH_2CN$), 3.77 (4×S, 12H, $OCH_{3\ (DMTr)}$), 3.73-3.51 (m, 8H, $OCH_2CH_2CN$, H5', $CH_{(iPr)}$), 3.48 (6H, $CH_{3\ (2'-O)}$), 3.37 (m, 2H, H5"), 2.63 (t, $^3J_{H,H}$=6.3 Hz, 2H, $OCH_2CH_2CN$), 2.38 (t, $^3J_{H,H}$=6.3 Hz, 2H, $OCH_2CH_2CN$), 1.20 (m, 18H, $CH_{3\ (iPr)}$), 1.08 (d, $^3J_{H,H}$=6.8 Hz, 6H, $CH_3$ (iPr)) ppm; $^{19}$F NMR (470.6 MHz, $D_2O$, NaF, 25° C.): δ=−137.8 (m, 1F, F), −140.0 (m, 1F, F) ppm; $^{31}$P NMR (202.5 MHz, $CDCl_3$, $H_3PO_4$, 25° C.): δ=150.9 (s, 1P, P), 150.4 (s, 1P, P) ppm;

Example 2: Synthesis of 5'-phosphorylated di- and trinucleotides (pA*pG or pA*pGpG)

Synthesis of dinucleotide was performed manually using a 10 mL syringe equipped with a frit filter. The solid support (5'-O-DMT-2'-O-TBDMS-$rG^{iBu}$ 3'-lcaa PrimerSupport 5G, GE Healthcare, 308 μmol/g) was placed in a syringe and washed with dry acetonitrile. In the coupling step, 1.2-1.5 equivalents of phosphoramidite (A*-CEP, G-CEP or bis-(2-cyanoethyl)-N,N-diisopropylphosphoramidite) dissolved in 1 mL of anhydrous acetonitrile and 1.5 mL of 0.30 M 5-(benzylthio)-1-H-tetrazole in acetonitrile were shaken for 15 min in a syringe capped with a plunger. A solution of 3% (v/v) trichloroacetic acid in dichloromethane was used as a detritylation reagent and 0.05 M iodine in pyridine/water ($9:1_{v/v}$) for oxidation. After the last cycle of synthesis, RNAs, still on the solid support, were treated with 20% (v/v) diethylamine in acetonitrile to remove 2-cyanoethyl protecting groups. Finally, the solid support was washed with acetonitrile and dried with argon. The product was cleaved from the solid support and deprotected with AMA (40% methylamine/33% ammonium hydroxide $1:1_{v/v}$; 55° C., 1 h), evaporated to dryness and redissolved in DMSO (200 μL). The TBDMS group was removed using triethylammonium trihydrofluoride (TEA-3HF; 250 μL, 65° C., 3 h), and then the mixture was cooled down and diluted with 0.25 M $NaHCO_3$ in water (20 mL). The product was isolated by ion-exchange chromatography on DEAE Sephadex (gradient elution 0-0.9 M TEAB) to afford after evaporation a triethylammonium salt of pA*pG dinucleotide. The yield was estimated by UV absorption at 260 nm, assuming the extinction coefficient ε=27.1 L/mmol/cm for dinucleotides or 39.0 L/mmol/cm for trinucleotides.

| Compound (pA*pG or pA*pGpG) | Chemical structure | Synthesis scale [μmol] | Yield[a] [μmol] | RP HPLC[b] $R_t$ [min] | $m/z_{calcd.}$ | $m/z_{meas.}$ |
|---|---|---|---|---|---|---|
| $p^{Bn6}A_mpG$ | 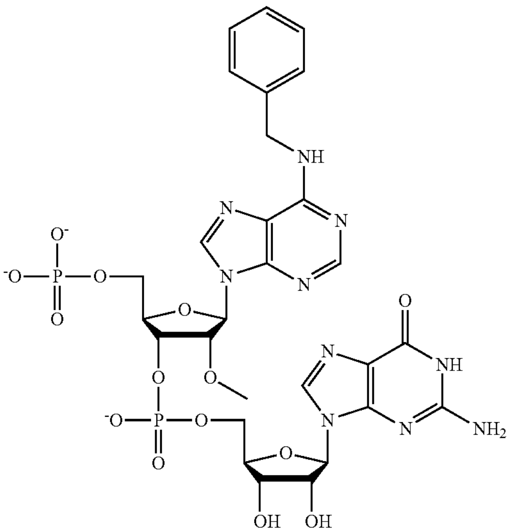 | 200 | 100.0 | 9.657 | 795.16584 | 795.16658 |
| $p^{2MeBn6}A_mpG$ | 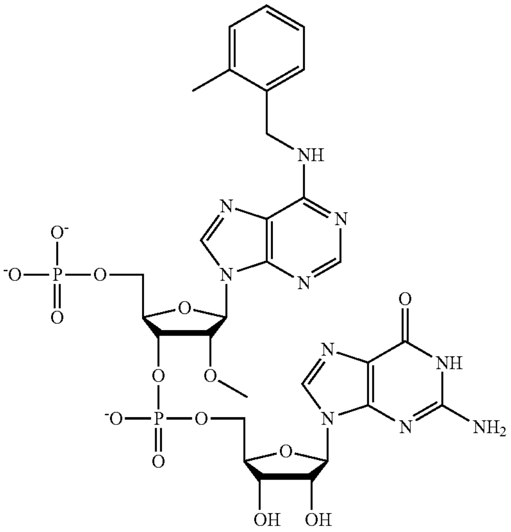 | 200 | 40.6 | 10.749 | 809.18149 | 809.18073 |

-continued
| Compound (pA*pG or pA*pGpG) | Chemical structure | Synthesis scale [μmol] | Yield[a] [μmol] | RP HPLC[b] $R_t$ [min] | $m/z_{calcd.}$ | $m/z_{meas.}$ |
|---|---|---|---|---|---|---|
| p$^{3MeBn6}$A$_m$pG | 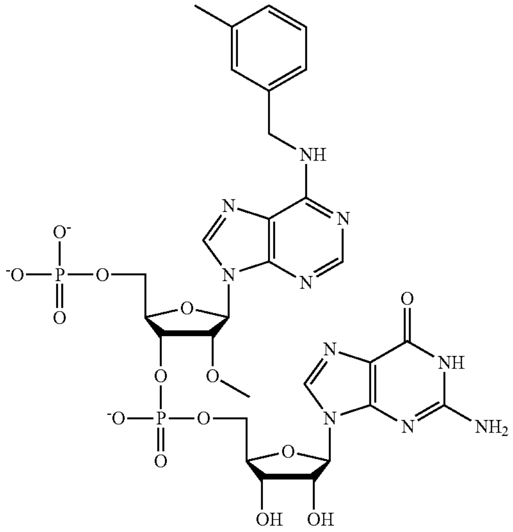 | 200 | 104.4 | 10.613 | 809.18149 | 809.18080 |
| p$^{4MeBn6}$A$_m$pG | 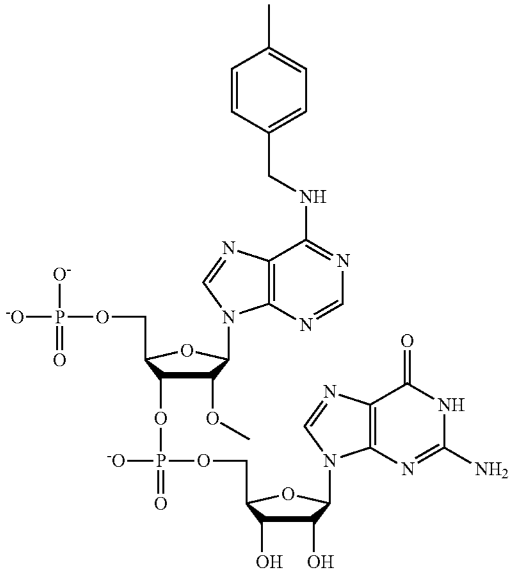 | 200 | 73.8 | 10.980 | 809.18149 | 809.18007 |

-continued
| Compound (pA*pG or pA*pGpG) | Chemical structure | Synthesis scale [μmol] | Yield[a] [μmol] | RP HPLC[b] $R_t$ [min] | $m/z_{calcd.}$ | $m/z_{meas.}$ |
|---|---|---|---|---|---|---|
| $p^{4FBn6}A_mpG$ | 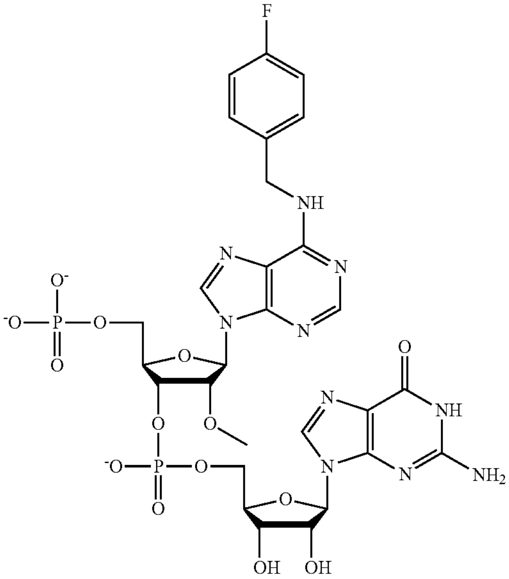 | 200 | 132.5 | 10.184 | 813.15642 | 813.15560 |
| $p^{3,4diFBn6}A_mpG$ | 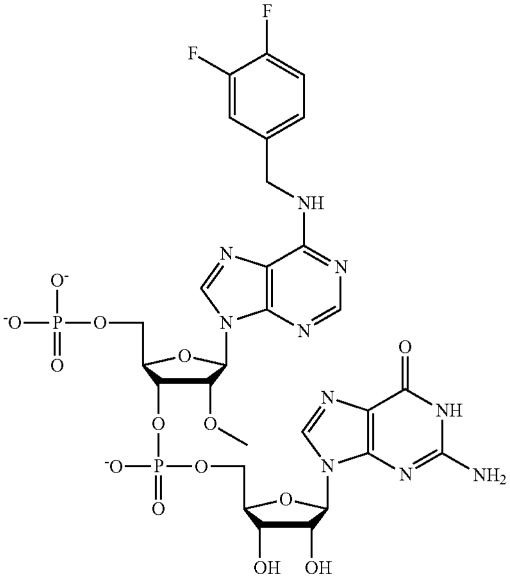 | 200 | 126.9 | 10.795 | 831.14700 | 831.14802 |

-continued
| Compound (pA*pG or pA*pGpG) | Chemical structure | Synthesis scale [μmol] | Yield[a] [μmol] | RP HPLC[b] $R_t$ [min] | $m/z_{calcd.}$ | $m/z_{meas.}$ |
|---|---|---|---|---|---|---|
| $p^{1Naphm6}A_mpG$ | 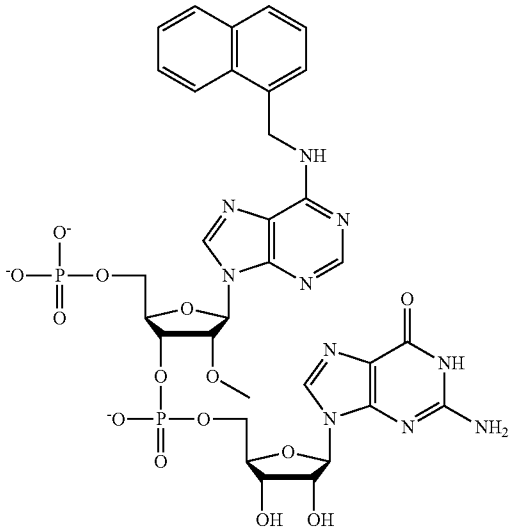 | 200 | 85.6 | 13.474 | 845.18149 | 845.18211 |
| $p^{2Naphm6}A_mpG$ | 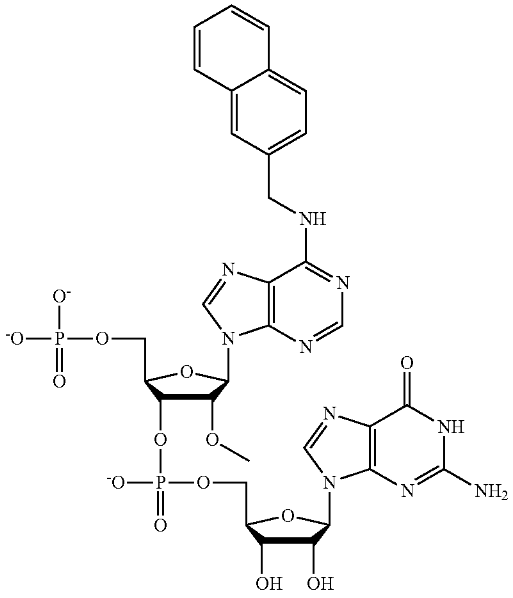 | 200 | 56.5 | 13.411 | 845.18149 | 845.18212 |

-continued

| Compound (pA*pG or pA*pGpG) | Chemical structure | Synthesis scale [μmol] | Yield[a] [μmol] | RP HPLC[b] $R_t$ [min] | $m/z_{calcd.}$ | $m/z_{meas.}$ |
|---|---|---|---|---|---|---|
| $p^{Bn6}A_m$pGpG | 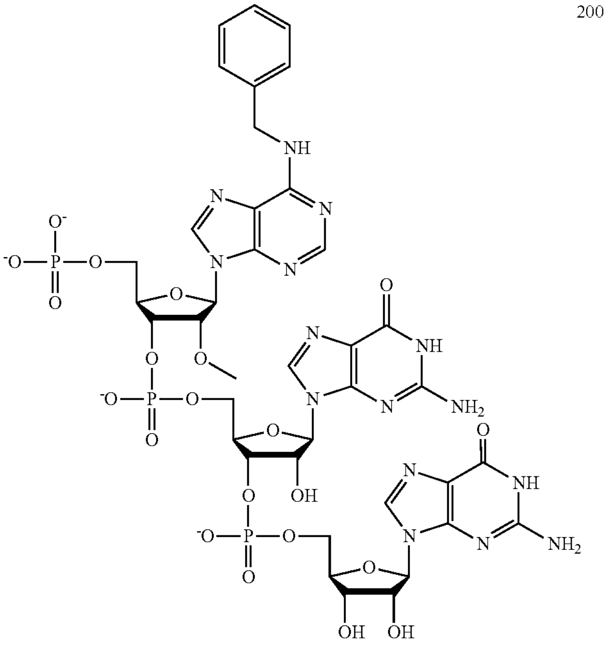 | 200 | 138 | 8.578 | 569.6 (z = 2) | 569.7 (z = 2) |

[a]after DEAE Sephadex;
[b]Gradient elution: 0-50% MeOH in aq. $CH_3COONH_4$ pH 5.9 within 75 min, then isocratically 50% MeOH in $CH_3COONH_4$;

$p^{2MeBn6}A_m$pG (TEAH$^+$): $^1$H NMR (500 MHz, $D_2O$, TMS, 25° C.): δ=8.41 (s, 1H, H$8_A$), 8.14 (s, 1H, H$2_A$), 7.93 (s, 1H, H$8_G$), 7.30-7.15 (m, 4H, ArH$_{2MeBn}$), 6.11 (d, $^3J_{H,H}$=5.1 Hz, 1H, H1'$_A$), 5.83 (d, $^3J_{H,H}$=5.2 Hz, 1H, H1'G), 4.92 (m, 1H, H3'$_A$), 4.76 (m, 2H, $CH_{2,\ Bn}$, overlapped with HDO), 4.72 (m, 1H, H2'$_G$), 4.50-4.47 (m, 2H, H2'$_A$, H3'$_G$), 4.46 (s, 1H, H4'$_A$), 4.34 (s, 1H, H4'$_G$), 4.25-4.17 (m, 2H, H5'$_G$, H5"$_G$), 4.12- 4.04 (m, 2H, H5'$_A$, H5"$_A$), 3.50 (s, 3H, $CH_{3,\ 2'\text{-}O(A)}$), 3.36-3.04 (m, $CH_{2,\ TEAH+}$), 2.36 (s, 3H, $CH_{3,\ 2MeBn}$), 1.27 (m, $CH_{3,\ TEAH+}$) ppm; $^{31}$P NMR (202.5 MHz, $D_2O$, $H_3PO_4$, 25° C.): δ=1.38 (s, 1P, $P_{5'\text{-}A}$), 0.04 (s, 1P, $P_{A\text{-}G}$) ppm;

$p^{4MeBn6}A_m$DG (TEAH+): $^1$H NMR (500 MHz, $D_2O$, TMS, 25° C.): δ=8.39 (s, 1H, H$8_A$), 8.14 (s, 1H, H$2_A$), 7.93 (s, 1H, H$8_G$), 7.27 (d, $^3J_{H,H}$=8.0 Hz, 2H, ArH$_{4MeBn(3\&5)}$), 7.18 (d, $^3J_{H,H}$=7.9 Hz, 2H, ArH$_{4MeBn(2\&6)}$), 6.10 (d, $^3J_{H,H}$=5.0 Hz, 1H, H1'$_A$), 5.83 (d, $^3J_{H,H}$=5.2 Hz, 1H, H1'$_G$), 4.92 (m, 1H, H3'$_A$), 4.79 (m, 2H, $CH_{2,\ Bn}$, overlapped with HDO), 4.72 (m, 1H, H2'$_G$), 4.50-4.45 (m, 3H, H2'$_A$, H3'$_G$, H4'$_A$), 4.34 (s, 1H, H4'$_G$), 4.25-4.17 (m, 2H, H5'G, H5"$_G$), 4.12-4.05 (m, 2H, H5'$_A$, H5"$_A$), 3.50 (s, 3H, $CH_{3,\ 2'\text{-}O[A]}$), 3.20 (q, $^3J_{H,H}$=7.3 Hz, $CH_{2,TEAH+}$), 2.29 (s, 3H, $CH_{3,2MeBn}$), 1.28 (t, $^3J_{H,H}$=7.3 Hz, $CH_{3,TEAH+}$) ppm; $^{31}$P NMR (202.5 MHz, $D_2O$, $H_3PO_4$, 25° C.): δ=1.06 (s, 1P, $P_{5'A}$), 0.05 (s, 1P, $P_{A\text{-}G}$) ppm;

$p^{1Naphm6}A_m$pG (TEAH+): $^1$H NMR (500 MHz, $D_2O$, TMS, 25° C.): δ=8.30 (s, 1H, H$8_A$), 8.07 (s, 1H, H$2_A$), 8.04 (m, 1H, ArH$_{Naph}$), 7.91 (s, 1H, H$8_G$), 7.88 (m, 1H, ArH$_{Naph}$), 7.80 (m, 1H, ArH$_{Naph}$), 7.57-7.40 (m, 4H, ArH$_{Naph}$), 6.05 (d, $^3J_{H,H}$=5.0 Hz, 1H, H1'$_A$), 5.80 (d, $^3J_{H,H}$=5.2 Hz, 1H, H1'$_G$), 5.17 (d, $^2J_{H,H}$=14.9 Hz, 1H, $CH_{2,\ Naphm}$), 5.05 (d, $^2J_{H,H}$=14.9 Hz, 1H, $CH_{2,\ Naphm}$), 4.92 (m, 1H, H3'$_A$), 4.71 (m, 1H, H2'$_G$), 4.50-4.45 (m, 3H, H2'$_A$, H3'$_G$, H4'$_A$), 4.34 (s, 1H, H4'$_G$), 4.26-4.17 (m, 2H, H5'$_G$, H5"$_G$), 4.09 (m, 2H, H5'$_A$, H5"$_A$), 3.51 (s, 3H, $CH_{3,\ 2'\text{-}O[A]}$), 3.33-3.03 (m, $CH_{2,\ TEAH+}$), 1.29-1.24 (m, $CH_{3,\ TEAH+}$) ppm; $^{31}$P NMR (202.5 MHz, $D_2O$, $H_3PO_4$, 25° C.): δ=1.39 (s, 1P, $P_{5\text{-}A}$), 0.06 (s, 1P, $P_{A\text{-}G}$) ppm;

$p^{2Naphm6}A_m$pG (TEAH+): $^1$H NMR (500 MHz, $D_2O$, TMS, 25° C.): δ=8.37 (s, 1H, H$8_A$), 8.02 (s, 1H, H$2_A$), 7.88 (s, 1H, H$8_G$), 7.78 (m, 2H, ArH$_{Naph}$), 7.71 (m, 2H, ArH$_{Naph}$), 7.43 (m, 3H, ArH$_{Naph}$), 5.97 (d, $^3J_{H,H}$=4.7 Hz, 1H, H1'$_A$), 5.78 (d, $^3J_{H,H}$=5.1 Hz, 1H, H1'G), 4.94-4.86 (m, 3H, H3'$_A$, $CH_{2,\ Naphm}$), 4.67 (m, 1H, H2'$_G$), 4.49-4.43 (m, 3H, H2'$_A$, H3'G, H4'$_A$), 4.33 (s, 1H, H4'$_G$), 4.25-4.16 (m, 2H, H5'$_G$, H5"$_G$), 4.11 (m, 2H, H5'$_A$, H5"$_A$), 3.49 (s, 3H, $CH_{3,2'\text{-}O(A)}$), 3.35-3.03 (m, $CH_{2,TEAH+}$), 1.29-1.24 (m, $CH_{3,TEAH+}$) ppm; $^{31}$P NMR (202.5 MHz, $D_2O$, $H_3PO_4$, 25° C.): δ=1.31 (s, 1P, $P_{5'A}$), 0.04 (s, 1P, $P_{A\text{-}G}$) ppm;

$p^{4FBn6}A_m$PG (TEAH$^+$): 1H NMR (500 MHz, $D_2O$, TMS, 25° C.): δ=8.40 (s, 1H, H$8_A$), 8.15 (s, 1H, H$2_A$), 7.93 (s, 1H, H$8_G$), 7.39 (m, 2H, ArH$_{4FBn}$), 7.09 (m, 2H, ArH$_{4FBn}$), 6.11 (d, $^3J_{H,H}$=5.1 Hz, 1H, H1'$_A$), 5.83 (d, $^3J_{H,H}$=5.2 Hz, 1H, H1'$_G$), 4.93 (m, 1H, H3'$_A$), 4.83 (m, 2H, $CH_{2,\ Bn}$, overlapped with HDO), 4.73 (m, 1H, H2'$_G$), 4.50-4.44 (m, 3H, H2'$_A$, H3'G, H4'$_A$), 4.35 (s, 1H, H4'$_G$), 4.25-4.17 (m, 2H, H5'$_G$, H5"$_G$), 4.12-4.04 (m, 2H, H5'$_A$, H5"$_A$), 3.50 (s, 3H, $CH_{3,\ 2'\text{-}O(A)}$), 3.20 (q, $^3J_{H,H}$=7.3 Hz, $CH_{2,\ TEAH+}$), 1.28 (t, $^3J_{H,H}$=7.3 Hz, $CH_{3,\ TEAH+}$) ppm; $^{31}$P NMR (202.5 MHz, $D_2O$, $H_3PO_4$, 25° C.): δ=1.08 (s, 1P, $P_{5'A}$), 0.06 (s, 1P, $P_{A\text{-}G}$) ppm;

$p^{3,4diFBn6}A_m$pG (TEAH$^+$): $^1$H NMR (500 MHz, $D_2O$, TMS, 25° C.): δ=8.42 (s, 1H, H$8_A$), 8.14 (s, 1H, H$2_A$), 7.92 (s, 1H, H$8_G$), 7.30-7.14 (m, 3H, ArH$_{3,4d6FBn}$), 6.12 (d, $^3J_{H,H}$=5.1 Hz, 1H, H1'$_A$), 5.83 (d, $^3J_{H,H}$=5.3 Hz, 1H, H1'$_G$), 4.93 (m, 1H, H3'$_A$), 4.83 (m, 2H, $CH_{2,\ Bn}$, overlapped with HDO), 4.74 (m, 1H, H2'$_G$), 4.51-4.45 (m, 3H, H2'$_A$, H3'$_G$, H4'$_A$), 4.35 (s, 1H, H4'$_G$), 4.26-4.17 (m, 2H, H5'G, H5"$_G$), 4.12-4.05 (m, 2H, H5'$_A$, H5"$_A$), 3.50 (s, 3H, $CH_{3,\ 2'-O(A)}$), 3.20 (q, $^3J_{H,H}$=7.3 Hz, $CH_{2,\ TEAH+}$), 1.28 (t, $^3J_{H,H}$=7.3 Hz, $CH_{3,\ TEAH+}$) ppm; $^{31}$P NMR (202.5 MHz, $D_2O$, $H_3PO_4$, 25° C.): δ=1.20 (s, 1P, $P_{5'A}$), 0.06 (s, 1P, $P_{A-G}$) ppm;

p$^{Bn6}$A$_m$pGpG (TEAH$^+$): $^1$H NMR (500 MHz, $D_2O$, TMS, 25° C.) δ=8.39 (s, 1H), 8.09 (s, 1H), 7.95 (s, 1H), 7.87 (s, 1H), 7.47-7.29 (m, 5H), 6.07 (d, J=5.3 Hz, 1H), 5.82 (d, J=5.5 Hz, 1H), 5.76 (d, J=5.0 Hz, 1H), 4.95-4.89 (m, 1H), 4.79 (1H, overlapped with HDO), 4.79 (1H, overlapped with HDO), 4.71 (t, J=5.5 Hz, 1H), 4.48 (t, J=5.3 Hz, 1H), 4.47-4.43 (m, 4H), 4.34-4.30 (m, 1H), 4.29-4.14 (m, 4H), 4.08-3.98 (m, 2H), 3.46 (s, 3H), 3.20 (q, J=7.3 Hz), 1.28 (t, J=7.3 Hz) ppm; $^{31}$P NMR (202 MHz, $D_2O$, $H_3PO_4$, 25° C.) δ=1.73-1.43 (m, 1P), 0.41-0.27 (m, 1P), −0.04-−0.13 (m, 1P) ppm.

Example 3: Synthesis of Trinucleotide Cap Analogs m$^7$GpppA*pG

Step 1. Activation of pNpG: Dinucleotide 5'-phosphate was dissolved in DMF (to obtain a 0.05 M solution) followed by addition of imidazole (16 equivalents), 2,2'-dithiodipiridine (6 equivalents), triethylamine (6 equivalents) and triphenylphosphine (6 equivalents). The mixture was stirred at room temperature for 2 h. The product was precipitated by addition of a solution of sodium perchlorate (10 equivalents) in acetonitrile (10 times the volume of DMF). The precipitate was centrifuged at 4° C., washed with cold acetonitrile 3 times and dried under reduced pressure to give a sodium salt of dinucleotide P-imidazolide (Im-pNpG).

Step 2. Formation of triphosphate bridge: 7-Methylguanosine 5'-diphosphate (m$^7$GDP; 1.5 equivalent) and Im-pNpG (1 equivalent) were suspended in DMF (to obtain a 0.05 M solution of P-imidazolide). Then $ZnCl_2$ (8 equivalents) were added and the mixture was stirred at room temperature for 2 h. The reaction was quenched by addition of a solution of $Na_2$EDTA (20 mg/mL; 8 equivalents) and $NaHCO_3$ (10 mg/mL) in water and the product was isolated by ion-exchange chromatography on DEAE Sephadex (gradient elution 0-1.2 M TEAB) to afford after evaporation a triethylammonium salt of m$^7$Gppp$^{bn6}$A$_m$pG. Additional purification by RP HPLC (C18) using a linear gradient of acetonitrile in aqueous $CH_3COONH_4$ buffer pH 5.9 provided (after repeated freeze-drying from water) an ammonium salt of m$^7$GpppA*pG. The yield was estimated by UV absorption at 260 nm, assuming the extinction coefficient ε=35.0 L/mmol/cm).

| Compound | Chemical structure |
|---|---|
| m$^7$GPPP$^{Bn6}$A$_m$pG | 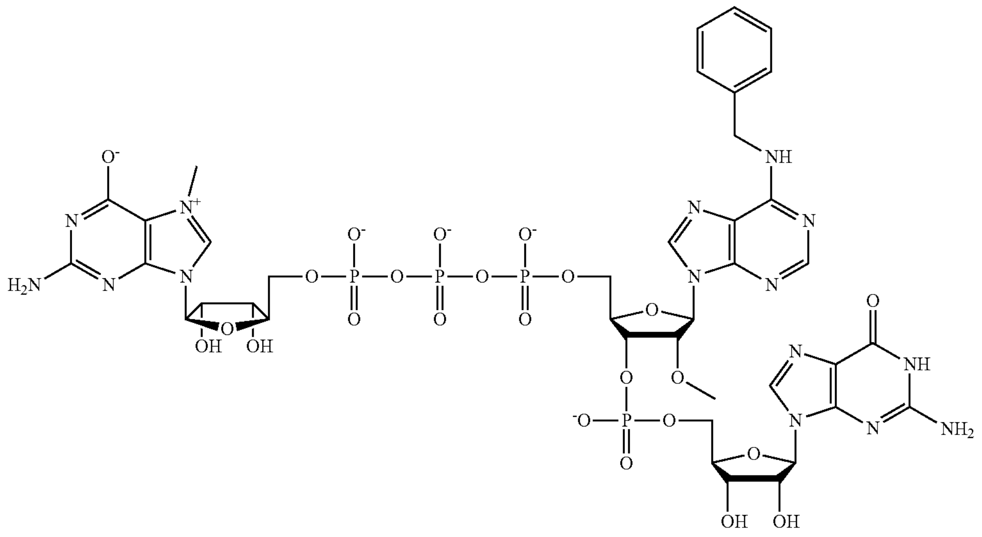 |

-continued
m7Gppp2meBn6AmPG
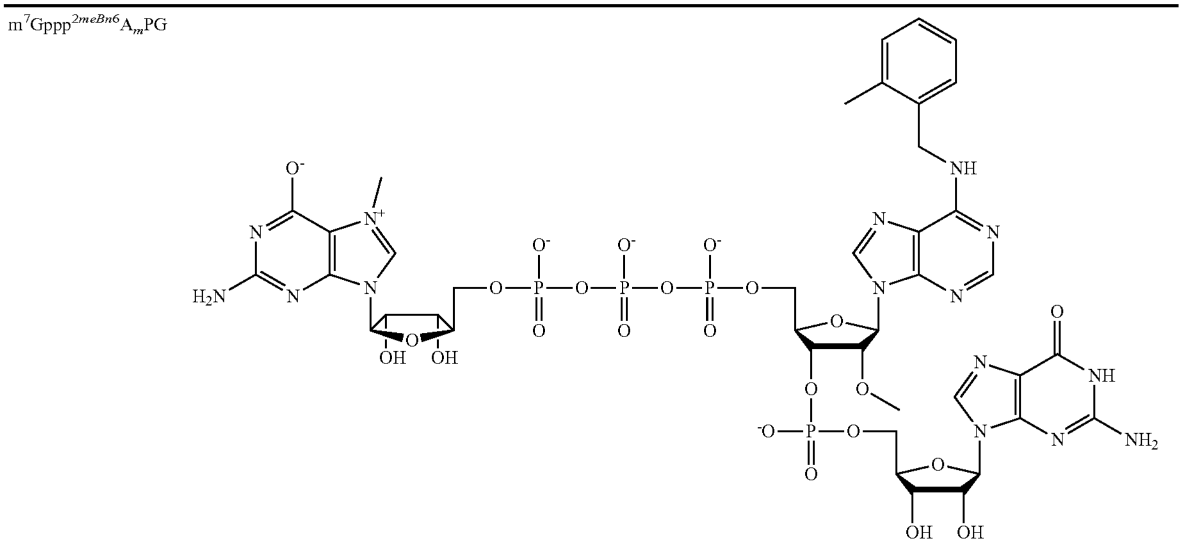
m7Gppp3MeBn6AmpG
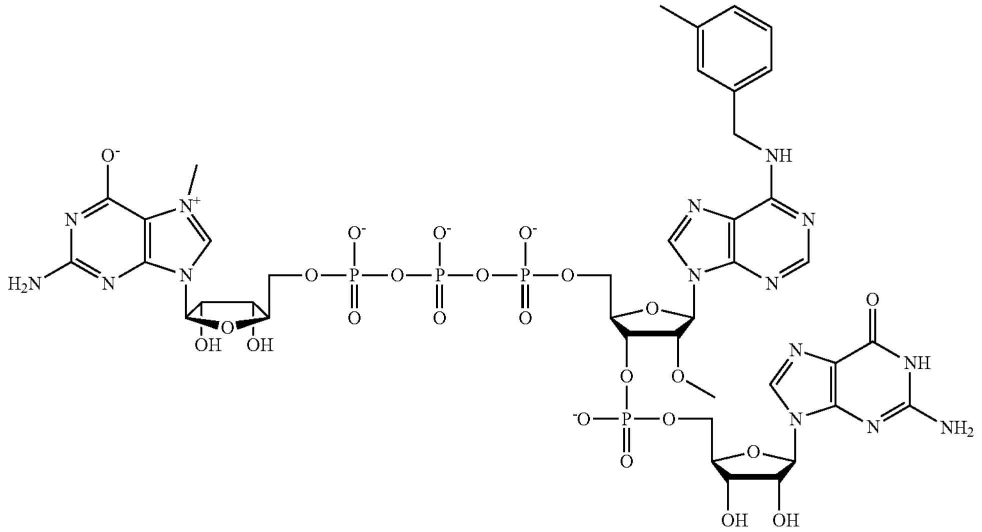
m7Gppp4MeBn6AmpG
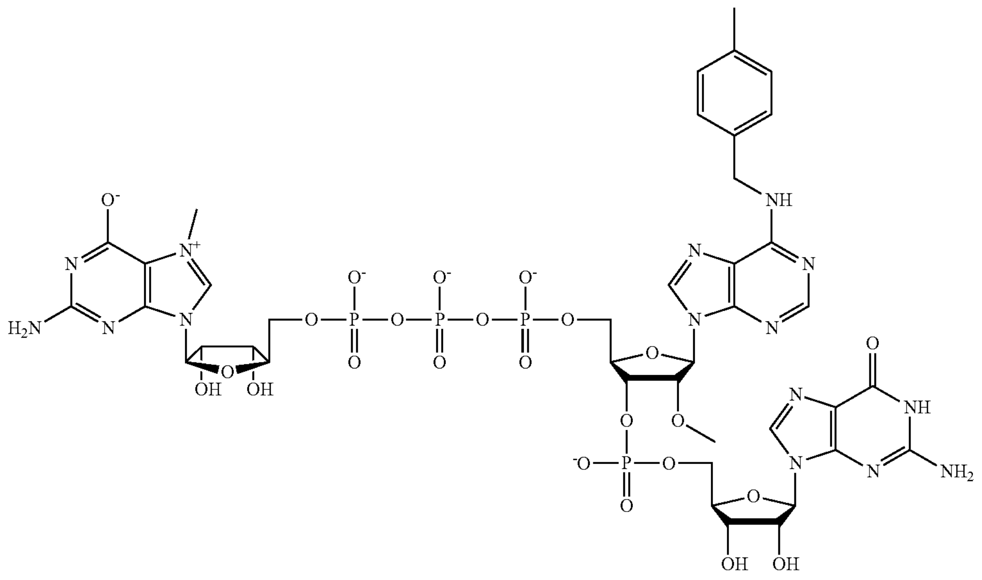

-continued
m$^7$Gppp$^{4FBn6}$A$_m$pG
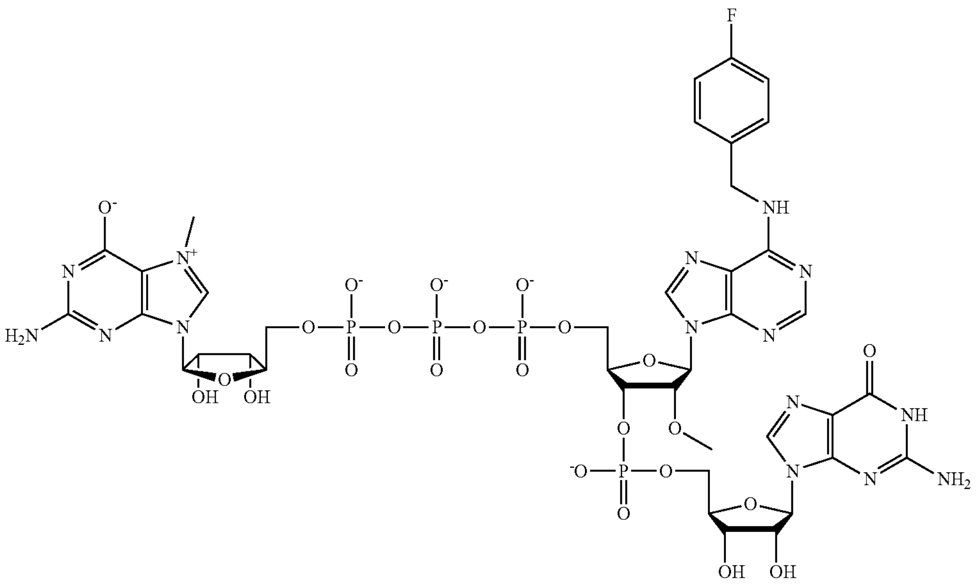
m$^7$Gppp$^{3,4diFBn6}$A$_m$pG
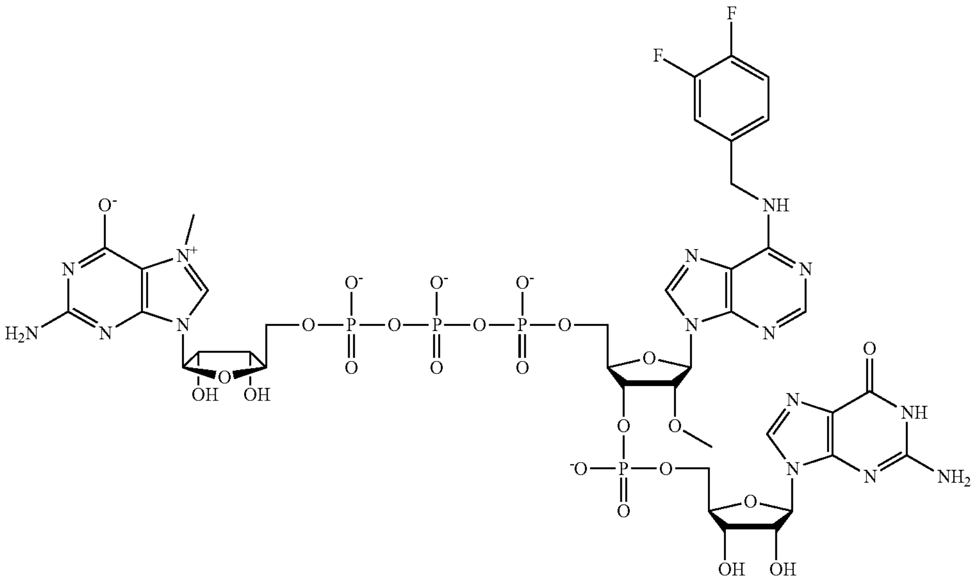

-continued $m^7Gppp^{1Naphm6}A_mpG$

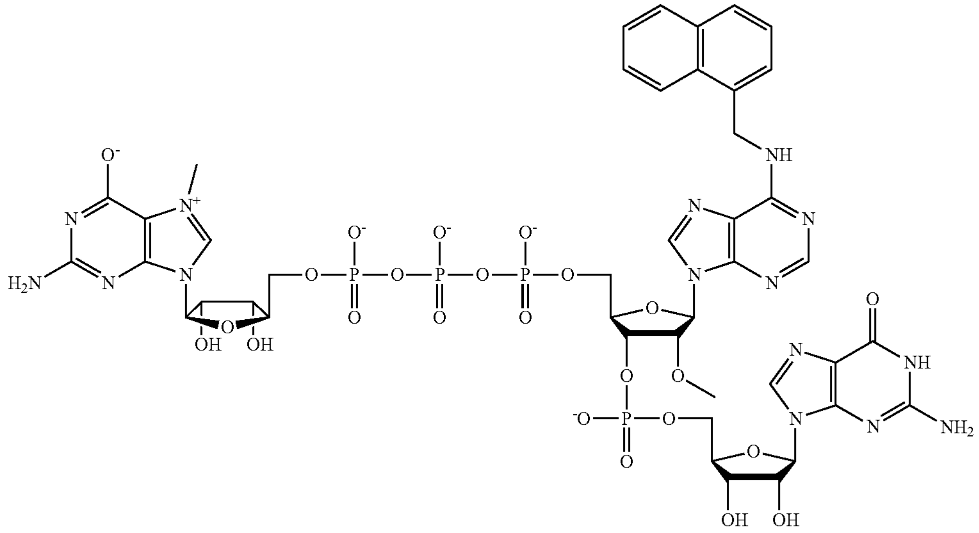

$m^7Gppp^{2Naphm6}A_mpG$

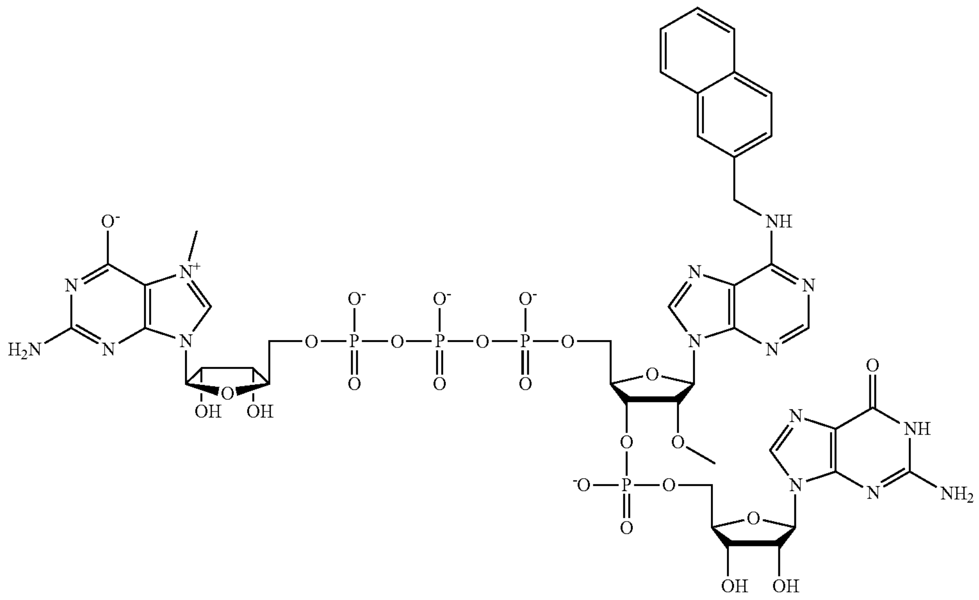

| Compound | Synthesis scale [µmol] | Yield[a] [µmol] | RP HPLC[b] $R_1$ [min] | m/z calc. for $[M-H]^-$ | m/z meas. |
|---|---|---|---|---|---|
| $m^7GPPP^{Bn6}A_mpG$ | 100.0 | 70.1 | 8.335 | 1234.19526 | 1234.19524 |
| $m^7Gppp^{2meBn6}A_mPG$ | 40.6 | 22.0 | 9.387 | 1248.21091 | 1248.21101 |
| $m^7Gppp^{3MeBn6}A_mpG$ | 104.4 | 31.6 | 9.193 | 1248.21091 | 1248.20887 |
| $m^7Gppp^{4MeBn6}A_mpG$ | 73.8 | 39.3 | 9.672 | 1248.21091 | 1248.21158 |
| $m^7Gppp^{4FBn6}A_mpG$ | 132.5 | 72.3 | 8.674 | 1252.18584 | 1252.18575 |
| $m^7Gppp^{3,4diFBn6}A_mpG$ | 126.9 | 84.7 | 9.133 | 1270.17641 | 1270.17669 |
| $m^7Gppp^{1Naphm6}A_mpG$ | 85.6 | 40.8 | 10.848 | 12484.21091 | 1284.21106 |
| $m^7Gppp^{2Naphm6}A_mpG$ | 56.5 | 25.1 | 10.812 | 1284.21091 | 1284.21071 |

[a]after RP HPLC;

[b]Gradient elution: 0-50% MeOH in aq. $CH_3COONH_4$ pH 5.9 within 7.5 min, then isocratically 50% MeOH in $CH_3COONH_4$;

$m^7Gppp^{Bn6}A_mpG$: $^1H$ NMR (500 MHz, $D_2O$, TMS, 25° C.): δ=9.06 (s, 1H, $H8_{m7G}$), 8.46 (s, 1H, $H8_A$), 8.19 (s, 1H, $H2_A$), 8.03 (s, 1H, $H8_G$), 7.44-7.31 (m, 5H, $ArH_{Bn}$), 6.03 (d, $^3J_{H,H}$=−5.6 Hz, 1H, $H1'_A$), 5.88 (d, $^3J_{H,H}$=3.7 Hz, 1H, $H1'_{m7G}$), 5.84 (d, $^3J_{H,H}$=5.8 Hz, 1H, $H1'_G$), 4.93 (m, 1H, $H3'_A$), 4.81 (m, 1H, $H2'_G$, overlapped with HDO), 4.85-4.74 (m, 2H, $CH_{2,\ Bn}$, overlapped with HDO), 4.59 (m, 1H, $H2'_{m7G}$), 4.53-4.49 (m, 2H, $H4'_A$, $H3'_G$), 4.48-4.44 (m, 2H, $H2'_A$, $H3'_{m7G}$), 4.38-4.16 (m, 8H, $H4'_{m7G}$, $H4'_G$, $H5'_{m7G}$, $H5''_{m7G}$, $H5'_A$, $H5''_A$, $H5'_G$, $H5''_G$), 4.02 (s, 3H, $CH_{3,m7G}$), 3.43 (s, 3H, $CH_{3,2'-O}$) ppm; $^{31}P$ NMR (202.5 MHz, $D_2O$, $H_3PO_4$, 25° C.): δ=0.03 (s, 1P, $P_{A-G}$), −10.58 (m, 2P, $P_\alpha$, $P_\gamma$), −21.98 (t, $^2J_{P,P}$=18.4 Hz, 1P, $P_\beta$) ppm;

$m^7GPpp^{2MeBn6}A_mpG$: $^1H$ NMR (500 MHz, $D_2O$, TMS, 25° C.): δ=9.08 (s, 1H, $H8_{m7G}$), 8.50 (s, 1H, $H8_A$), 8.21 (s, 1H, $H2_A$), 8.06 (s, 1H, $H8_G$), 7.29-7.12 (m, 4H, $ArH_{2MeBn}$), 6.04 (d, $^3J_{H,H}$=5.5 Hz, 1H, H1'$_A$), 5.89 (d, $^3J_{H,H}$=3.4 Hz, 1H, H1'$_{m7G}$), 5.85 (d, $^3J_{H,H}$=5.6 Hz, 1H, H1'$_G$), 4.95 (m, 1H, H3'$_A$), 4.81 (m, 1 H, H2'$_G$, overlapped with HDO), 4.75 (m, 2H, $CH_{2,\ Bn}$, overlapped with HDO), 4.59 (m, 1H, H2'$_{m7G}$), 4.54-4.44 (m, 4H, H2'$_A$, H3'$_{m7G}$, H3'$_G$, H4'$_A$), 4.38-4.15 (m, 8H, H4'$_{m7G}$, H4'$_G$, H5'$_{m7G}$, H5"$_{m7G}$, H5'$_A$, H5"$_A$, H5'$_G$, H5"$_G$), 4.02 (s, 3H, $CH_{3,\ m7G}$), 3.43 (s, 3H, $CH_3$, 2.0), 2.34 (s, 3H, $CH_{3,\ 2MeBn}$) ppm; $^{31}$P NMR (202.5 MHz, $D_2O$, $H_3PO_4$, 25° C.): δ=0.04 (s, 1P, $P_{A-G}$), −10.56 (m, 2P, $P_\alpha$, $P_\gamma$), −21.98 (m, 1P, $P_\beta$) ppm;

m$^7$Gppp$^{3MeBn6}$A$_m$pG: $^1$H NMR (500 MHz, $D_2O$, TMS, 25° C.): δ=9.07 (s, 1H, H8$_{m7G}$), 8.48 (s, 1H, H8$_A$), 8.20 (s, 1H, H2$_A$), 8.04 (s, 1H, H8$_G$), 7.29-7.12 (m, 4H, $ArH_{3MeBn}$), 6.03 (d, $^3J_{H,H}$=5.5 Hz, 1H, H1'$_A$), 5.88 (d, $^3J_{H,H}$=−3.5 Hz, 1H, H1'$_{m7G}$), 5.84 (d, $^3J_{H,H}$=5.7 Hz, 1H, H1'$_G$), 4.93 (m, 1H, H3'$_A$), 4.83 (m, 1H, H2'$_G$, overlapped with HDO), 4.76 (m, 2H, $CH_{2,\ Bn}$, overlapped with HDO), 4.58 (m, 1H, H2'$_{m7G}$), 4.52-4.44 (m, 4H, H2'$_A$, H3'$_{m7G}$, H3'$_G$, H4'$_A$), 4.38-4.15 (m, 8H, H4'$_{m7G}$, H4'G, H5'$_{m7G}$, H5"$_{m7G}$, H5'$_A$, H5"$_A$, H5'$_G$, H5"$_G$), 4.01 (s, 3H, $CH_{3,\ m7G}$), 3.42 (s, 3H, $CH_{3,\ 2'-O}$), 2.27 (s, 3H, $CH_{3,\ 2MeBn}$) ppm; $^{31}$P NMR (202.5 MHz, $D_2O$, $H_3PO_4$, 25° C.): δ=0.02 (s, 1P, $P_{A-G}$), −10.60 (m, 2P, $P_\alpha$, $P_\gamma$) −22.00 (t$^2J_{P,P}$=18.4 Hz, 1P, $P_\beta$) ppm;

m$^7$Gppp$^{4MeBn6}$A$_m$pG: $^1$H NMR (500 MHz, $D_2O$, TMS, 25° C.): δ=9.07 (s, 1H, H8$_{m7G}$), 8.49 (S, 1H, H8$_A$), 8.19 (s, 1H, H2$_A$), 8.06 (s, 1H, H8$_G$), 7.22 (m, 2H, $ArH_{4MeBn}$), 7.11 (m, 2H, $ArH_{4MeBn}$), 6.02 (d, $^3J_{H,H}$=5.4 Hz, 1H, H1'$_A$), 5.88 (d, $^3J_{H,H}$=3.6 Hz, 1H, H1'$_{m7G}$), 5.84 (d, $^3J_{H,H}$=5.6 Hz, 1H, H1'$_G$), 4.94 (m, 1H, H3'$_A$), 4.79 (m, 1H, H2'$_G$, overlapped with HDO), 4.71 (m, 2H, $CH_{2,\ Bn}$), 4.58 (m, 1H, H2'$_{m7G}$), 4.54-4.48 (m, 2H, H3'$_G$, H4'$_A$), 4.45 (m, 2H, H2'$_A$, H3'$_{m7G}$), 4.39-4.16 (m, 8H, H4'$_{m7G}$, H4'$_G$, H5'$_{m7G}$, H5"$_{m7G}$, H5'$_A$, H5"$_A$, H5'$_G$, H5"$_G$), 4.01 (s, 3H, $CH_{3,\ m7G}$), 3.44 (s, 3H, $CH_{3,\ 2'-O}$), 2.24 (s, 3H, $CH_{3,\ 2MeBn}$) ppm; $^{31}$P NMR (202.5 MHz, $D_2O$, $H_3PO_4$, 25° C.): δ=0.02 (s, 1P, $P_{A-G}$), −10.56 (m, 2P, $P_\alpha$, $P_\gamma$), −21.92 (m, 1P, $P_\beta$) ppm;

m$^7$Gppp$^{1Naphm6}$A$_m$pG: $^1$H NMR (500 MHz, $D_2O$, TMS, 25° C.): δ=8.97 (s, 1H, H8$_{m7G}$), 8.33 (s, 1H, H8$_A$), 8.03 (s, 2H, H2$_A$, H8$_G$), 7.80-7.25 (m, 7H, $ArH_{Naph}$), 5.94 (m, 1H, H1'$_A$), 5.79 (d, $^3J_{H,H}$=5.3 Hz, 1H, H1'$_G$), 5.73 (m, 1H, H1'$_{m7G}$), 4.97 (m, 1H, H3'$_A$), 4.83 (m, 2H, $CH_{2,\ Bn}$, overlapped with HDO), 4.73 (m, 1H, H2'$_G$), 4.54 (m, 1H, H4'$_A$), 4.51-4.17 (m, 12H, H2'$_{m7G}$, H2'$_A$, H3'$_{m7G}$, H3'$_G$, H4'$_{m7G}$, H4'$_G$, H5'$_{m7G}$, H5"$_{m7G}$, H5'$_A$, H5"$_A$, H5'$_G$, H5"$_G$), 3.84 (s, 3H, $CH_{3,m7G}$), 3.50 (s, 3H, $CH_{3,2'-O}$) ppm; $^{31}$P NMR (202.5 MHz, $D_2O$, $H_3PO_4$, 25° C.): δ=0.02 (s, 1P, $P_{A-G}$), −10.56 (m, 2P, $P_\alpha$, $P_\gamma$), −21.85 (m, 1P, $P_\beta$) ppm;

m$^7$Gppp$^{2Naphm6}$A$_m$pG: $^1$H NMR (500 MHz, $D_2O$, TMS, 25° C.): δ=8.93 (s, 1H, H8$_{m7G}$), 8.46 (s, 1H, H8$_A$), 8.04 (s, 2H, H2$_A$, H8$_G$), 7.72-7.19 (m, 7H, $ArH_{Naph}$), 5.89 (m, 1H, H1'$_A$), 5.79 (d, $^3J_{H,H}$=5.3 Hz, 1H, H1'$_G$), 5.71 (m, 1H, H1'$_{m7G}$), 4.97 (m, 1H, H3'$_A$), 4.83 (m, 2H, $CH_{2,\ Bn}$, overlapped with HDO), 4.71 (m, 1H, H2'$_G$), 4.54 (m, 1H, H4'$_A$), 4.51-4.16 (m, 12H, H2'$_{m7G}$, H2'$_A$, H3'$_{m7G}$, H3'$_G$, H4'$_{m7G}$, H4'$_G$, H5'$_{m7G}$, H5"$_{m7G}$, H5'$_A$, H5"$_A$, H5'$_G$, H5"$_G$), 3.77 (s, 3H, $CH_{3,\ m7G}$), 3.49 (S, 3H, $CH_{3,2'-O}$) ppm; $^{31}$P NMR (202.5 MHz, $D_2O$, $H_3PO_4$, 25° C.): δ=0.03 (s, 1P, $P_{A-G}$), -10.56 (m, 2P, $P_\alpha$, $P_\gamma$), −21.75 (m, 1P, $P_\beta$) ppm;

m$^7$Gppp$^{4FBn6}$A$_m$pG: $^1$H NMR (500 MHz, $D_2O$, TMS, 25° C.): δ=9.08 (s, 1H, H8$_{m7G}$), 8.47 (s, 1H, H8$_A$), 8.19 (s, 1H, H2$_A$), 8.05 (s, 1H, H8$_G$), 7.38 (m, 2H, $ArH_{4FBn}$), 7.06 (m, 2H, $ArH_{4FBn}$), 6.03 (d, $^3J_{H,H}$=5.5 Hz, 1H, H1'$_A$), 5.88 (d, $^3J_{H,H}$=3.3 Hz, 1H, H1'$_{m7G}$), 5.84 (d, $^3J_{H,H}$=5.7 Hz, 1H, H1'$_G$), 4.94 (m, 1H, H3'$_A$), 4.81 (m, 1H, H2'$_G$, overlapped with HDO), 4.84-4.74 (m, 2H, $CH_{2,\ Bn}$, overlapped with HDO), 4.58 (m, 1H, H2'$_{m7G}$), 4.54-4.48 (m, 2H, H3'$_G$, H4'$_A$), 4.46 (m, 2H, H2'$_A$, H3'$_{m7G}$), 4.39-4.15 (m, 8H, H4'$_{m7G}$, H4'$_G$, H5'$_{m7G}$, H5"$_{m7G}$, H5'$_A$, H5"$_A$, H5'$_G$, H5"$_G$), 4.02 (s, 3H, $CH_{3,\ m7G}$), 3.43 (s, 3H, $CH_{3,\ 2'-O}$) ppm; $^{19}$F NMR (470.6 MHz, $D_2O$, NaF, 25° C.): δ=−115.35 (s, 1F, F) ppm; $^{31}$P NMR (202.5 MHz, $D_2O$, $H_3PO_4$, 25° C.): δ=0.04 (s, 1P, $P_{A-G}$), -10.58 (m, 2P, $P_\alpha$, $P_\gamma$), −21.99 (m, 1P, $P_\beta$) ppm;

m$^7$Gppp$^{3,4diFBn6}$A$_m$pG: $^1$H NMR (500 MHz, $D_2O$, TMS, 25° C.): δ=9.09 (s, 1H, H8$_{m7G}$), 8.48 (s, 1H, H8$_A$), 8.19 (s, 1H, H2$_A$), 8.08 (s, 1H, H8$_G$), 7.30-7.14 (m, 3H, $ArH_{3,4diFBn}$), 6.03 (d, $^3J_{H,H}$=5.6 Hz, 1H, H1'$_A$), 5.88 (d, $^3J_{H,H}$=3.6 Hz, 1H, H1'$_{m7G}$), 5.85 (d, $^3J_{H,H}$=5.7 Hz, 1H, H1'$_G$), 4.94 (m, 1H, H3'$_A$), 4.81 (m, 1H, H2'$_G$, overlapped with HDO), 4.80 (m, 2H, $CH_{2,\ Bn}$, overlapped with HDO), 4.59 (m, 1H, H2'$_{m7G}$), 4.52 (m, 1H, H4'$_A$), 4.50 (m, 1H, H3'$_G$), 4.48-4.44 (m, 2H, H2'$_A$, H3'$_{m7G}$), 4.38-4.16 (m, 8H, H4'$_{m7G}$, H4', H5'$_{m7G}$, H5"$_{m7G}$, H5'$_A$, H5"$_A$, H5'$_G$, H5"$_G$), 4.02 (s, 3H, $CH_{3,\ m7G}$), 3.43 (s, 3H, $CH_{3,\ 2'-O}$) ppm; $^{19}$F NMR (470.6 MHz, $D_2O$, NaF, 25° C.): δ=−138.22 (s, 1F, F), −140.39 (s, 1F, F) ppm; $^{31}$P NMR (202.5 MHz, $D_2O$, $H_3PO_4$, 25° C.): δ=0.03 (s, 1P, $P_{A-G}$), −10.58 (m, 2P, $P_\alpha$, $P_\gamma$), −21.97 (m, 1P, $P_\beta$) ppm;

Example 4: Synthesis of p-phosphorothioate trinucleotide cap analog m$^7$Gppsp$^{Bn6}$A$_m$pG Step 1. Activation of p$^{Bn6}$A$_m$pG: Dinucleotide 5'-phosphate p$^{Bn6}$A$_m$pG (615 $mOD_{260\ nm}$, 22.7 μmol) was dissolved in DMF (400 μL) followed by addition of imidazole (24.7 mg, 363 μmol), 2,2'-dithiodipiridine (30 mg, 136 μmol), triethylamine (9.5 μL, 68 μmol) and triphenylphosphine (35.7 mg, 136 μmol). The mixture was stirred at room temperature for 48 h. The product was precipitated by addition of a solution of lithium perchlorate (24.1 mg, 227 μmol) in acetonitrile (4.0 mL). The precipitate was centrifuged at 4° C., washed with cold acetonitrile 3 times and dried under reduced pressure to give a lithium salt of dinucleotide P-imidazolide Im-p$^{Bn6}$A$_m$pG (19 mg).

Step 2. Formation of triphosphate bridge: 7-Methylguanosine β-thiodiphosphate m$^7$GDP-β-S (378 $mOD_{260\ nm}$, 33.2 μmol; obtained as described earlier and stored in TEAB at −20° C.)[12] was evaporated to dryness and suspended in DMF (890 μL). Then $ZnCl_2$ (24.1 mg, 177 μmol) and Im-p$^{Bn6}$A$_m$pG (19 mg) were added and the mixture was stirred at room temperature for 2 h. The reaction was quenched by addition of a solution of $Na_2EDTA$ (72.5 mg) and $NaHCO_3$ (36 mg) in water (3.6 mL) and the product was isolated by ion-exchange chromatography on DEAE Sephadex (gradient elution 0-1.2 M TEAB) to afford after evaporation triethylammonium salt of m$^7$Gppsp$^{Bn6}$A$_m$pG. Additional purification by RP HPLC (C18) using a linear gradient of acetonitrile in aqueous $CH_3COONH_4$ buffer pH 5.9 provided (after repeated freeze-drying from water) a P-diastereomeric mixture of m$^7$GppSp$^{Bn6}$A$_m$pG (217 $mOD_{260\ nm}$, 6.8 μmol, 31%) as an ammonium salt.

m$^7$Gppsp$^{Bn6}$A$_m$pG: RP HPLC (gradient elution 0-50% MeOH in $CH_3COONH_4$ pH 5.9 in 7.5 min, then isocratically): $R_t$=8,311 min; HRMS ESI(−): m/z 1250.17041 (calcd. for $C_{39}H_{48}N_{15}O_{23}P_4S$-[M-H]$^-$ 1250.17241); $^1$H NMR (500 MHz, $D_2O$, TMS, 25° C.): δ=9.13 (s, 1H, H8$_{m7G}$), 8.55 (s, 1H, H8$_A$), 8.22 (s, 1H, H2$_A$), 8.07 (s, 1H, H8$_G$), 7.41-7.25 (m, 5H, $ArH_{Bn}$), 6.05 (2×d, $^3J_{H,H}$=5.9 Hz, 1H, H1'$_A$), 5.91 (2×d, $^3J_{H,H}$=3.7 Hz, 1H, H1'$_{m7G}$), 5.85 (d, $^3J_{H,H}$=5.6 Hz, 1H, H1'$_G$), 5.00 (m, 1H, H3'$_A$), 4.81 (m, 1H, H2'$_G$ overlapped with HDO), 4.85-4.73 (m, 2H, $CH_{2,\ Bn}$, overlapped with HDO), 4.63 (m, 1H, H2'$_{m7G}$), 4.58-4.49 (m, 4H, H2'$_A$, H3'$_{m7G}$, H3'$_G$, H4'$_A$), 4.42-4.16 (m, 8H, H4'$_{m7G}$, H4'$_G$, H5'$_{m7G}$, H5"$_{m7G}$, H5'$_A$, H5"$_A$, H5'$_G$, H5"$_G$), 4.04-4.01 (2×S, 3H, $CH_{3,\ m7G}$), 3.45-3.43 (2×s, 3H, $CH_{3,2'-O}$) ppm; $^{31}$P NMR (202.5 MHz, $D_2O$, $H_3PO_4$, 25° C.): δ=30.92 (m, 1P, $P_β$), 0.06-0.01 (2×s, 1P, $P_{A-G}$), −11.45 (m, 2P, $P_α$, $P_γ$) ppm;

Example 5: Synthesis of 5'-phosphorothiolate trinucleotide cap analog $m^7Gppp^{5'S,Bn6}A_m pG$ Step 1. Synthesis of $p^{Bn6,5'S}A_m pG$: Synthesis of dinucleotide was performed manually using a 10 mL syringe equipped with a frit filter. The solid support (5'-O-DMT-2'-O-TBDMS-$rG^{iBu}$ 3'. Icaa PrimerSupport 5G, GE Healthcare, 308 μmol/g, 650 mg) was placed in a syringe and washed with dry acetonitrile. In the coupling step, 1.2-1.5 equivalents of $^{Bn6}A_m$ phosphoramidite dissolved in 1 mL of anhydrous acetonitrile and 1.5 mL of 0.30 M 5-(benzylthio)-1-H-tetrazole in acetonitrile were shaken for 30 min in a syringe capped with a plunger. A solution of 3% (v/v) trichloroacetic acid in dichloromethane was used as a detritylation reagent and 0.05 M iodine in pyridine/water ($9:1_{v/v}$) for oxidation. After the last cycle of synthesis, the support was treated with 20% (v/v) diethylamine in acetonitrile to remove 2-cyanoethyl protecting groups, washed with acetonitrile and dried with argon. Dinucleotide, still on a solid support, was then converted into 5'-iodo derivative by shaking the support with a solution of triphenoxymethylphosphonium iodide (1.08 g) in DMF (5 mL) for 15 minutes. The resin was then washed with DMF (15 mL) and acetonitrile (50 ml), dried and transferred to a flask containing a cold solution of triethylammonium thiophosphate (ca. 0.15 M) and triethylamine (0.30 M) in DMF (4 mL). The slurry was shaken at 2-4° C. overnight, filtered and washed with DMF (15 mL) and then acetonitrile (50 mL). The product was cleaved and deprotected using AMA (methylamine/ammonium hydroxide $1:1_{v/v}$; 55° C., 1 h) and isolated by ion-exchange chromatography on DEAE Sephadex (gradient elution 0-0.9 M TEAB) to afford after evaporation a triethylammonium salt of $p^{5'S,Bn6}A_m pG$ (2400 mOD, 88.5 μmol).

Step 2. Activation of $p^{Bn6,5'S}A_m pG$: Dinucleotide 5'-phosphorothiolate $p^{Bn6,5'S}A_m pG$ (2400 $mOD_{260\ nm}$, 88.5 μmol) was dissolved in DMF (1.80 mL) followed by addition of imidazole (96.3 mg, 1.42 mmol), 2,2'-dithiodipiridine (117 mg, 531 μmol), triethylamine (74.2 μL, 531 μmol) and triphenylphosphine (139 mg, 531 μmol). The mixture was stirred at room temperature for 2 h. The product was precipitated by addition of a solution of sodium perchlorate (108 mg, 885 μmol) in cold acetonitrile (20 mL). The precipitate was centrifuged at 4° C., washed with cold acetonitrile 3 times and dried under reduced pressure to give a sodium salt of dinucleotide P-imidazolide Im-$p^{bn6}A_m pG$ (92.2 mg).

Step 3. Formation of triphosphate bridge: 7-Methylguanosine 5'-diphosphate ($m^7GDP$; 1210 $mOD260_{nm}$, 106 μmol) and Im-$p^{5'S,Bn6}A_m pG$ (92.2 mg) were suspended in DMF (1.77 mL). Then $ZnCl_2$ (144 mg, 1.06 mmol) were added and the mixture was stirred at room temperature for 2 h. The reaction was quenched by addition of a solution (3 mL) of $Na_2EDTA$ (20 mg/mL) and $NaHCO_3$ (10 mg/mL) in water and the product was isolated by ion-exchange chromatography on DEAE Sephadex (gradient elution 0-1.2 M TEAB) to afford after evaporation triethylammonium salt of $m^7Gppp^{5'S,Bn6}A_m pG$, contaminated with a 2'-O-TBDMS protected cap $m^7Gppp^{5'S,Bn6}A_m pG_{TBDMS}$. To remove the TBDMS group, the solid was dissolved in DMSO (150 μL) and TEA (133 μL) followed by addition of TEA-3HF (78 μL). The mixture was shaken at 60° C. for 1 h and the reaction was quenched by addition of water (15 mL). The product was isolated by ion-exchange chromatography on DEAE Sephadex (gradient elution 0-1.2 M TEAB) and additionally purified by RP HPLC (C18) using a linear gradient of acetonitrile in aqueous $CH_3COONH_4$ buffer pH 5.9 to give (after repeated freeze-drying from water) an ammonium salt of $m^7Gppp^{5'S,Bn6}A_m pG$ (1530 mOD, 47.7 μmol).

$m^7GPPp^{5'S,Bn6}A_m pG$: RP HPLC (gradient elution 0-50% MeOH in $CH_3COONH_4$ pH 5.9 in 7.5 min, then isocratically): $R_t$=8.496 min; HRMS ESI(−): m/z 1250.17363 (calcd. for $C_{39}H_{48}N_{15}O_{23}P_4S^-$ [M-H]$^-$ 1250.17241); $^1H$ NMR (500 MHz, $D_2O$, TMS, 25° C.): δ=9.08 (s, 1H, $H8_{m7G}$), 8.37 (s, 1H, $H8_A$), 8.22 (s, 1H, $H2_A$), 8.11 (s, 1H, $H8_G$), 7.43-7.25 (m, 5H, $ArH_{Bn}$), 6.00 (d, $^3J_{H,H}$=5.8 Hz, 1H, $H1'_A$), 5.89 (d, $^3J_{H,H}$=2.9 Hz, 1H, $H1'_{m7G}$), 5.86 (d, $^3J_{H,H}$=5.5 Hz, 1H, $H1'_G$), 4.86 (m, 1H, $H3'_A$), 4.80 (m, 1H, $H2'_G$, overlapped with HDO), 4.78 (m, 2H, $CH_{2,\ Bn}$, overlapped with HDO), 4.58 (m, 1H, $H2'_{m7G}$), 4.56-4.49 (m, 3H, $H2'_A$, $H3'_G$, $H4'_A$), 4.47 (m, 1H, $H3'_{m7G}$), 4.42-4.18 (m, 6H, $H4'_{m7G}$, $H4'_G$, $H5'_{m7G}$, $H5''_{m7G}$, $H5'_G$, $H5''_G$), 4.02 (s, 3H, $CH_{3,\ m7G}$), 3.40 (s, 3H, $CH_{3,2'-O}$), 3.33 (m, 2H, $H5'_A$, $H5''_A$) ppm; $^{31}P$ NMR (202.5 MHz, $D_2O$, $H_3PO_4$, 25° C.): δ=8.19 (m, 1P, $P_α$), −0.09 (s, 1P, $P_{A-G}$), −10.59 (m, 1P, $P_γ$), −22.67 (m, 1P, $P_α$) ppm;

Example 6: Synthesis of tetranucleotide cap analog ($m^7GpppBn^6A_m pGpG$)

Step 1. Synthesis of Im-pBn6AmpGpG: Triethylammonium salt of $p^{Bn6}A_m pGpG$ (5366 $mOD_{260\ nm}$, 138 μmol) was dissolved in DMF (2800 μL) followed by addition of imidazole (150 mg, 2201 μmol), 2,2'-dithiodipiridine (182 mg, 826 μmol), triethylamine (84 μL, 826 μmol) and triphenylphosphine (216 mg, 826 μmol). The mixture was stirred at room temperature for 2 h and then the product was precipitated by addition of a cold solution of sodium perchlorate (169 mg, 1376 μmol) in acetonitrile. The precipitate was centrifuged at 4° C., washed with cold acetonitrile 3 times and dried under reduced pressure over $P_2O_5$ to give a sodium salt of Im-$pBn^6A_m pGpG$ (183 mg).

Im-$p^{Bn6}A_m pGpG$: RP-HPLC (gradient elution 0-50% MeOH in $CH_3COONH_4$ pH 5.9 in 7.5 min, then isocratically): $R_t$=8.865 min;

Step 2. Synthesis of $m^7Gppp^{Bn6}A_m pGpG$: The sodium salt of Im-$p^{bn6}A_m pGpG$ (5366 $mOD_{260\ nm}$, 138 μmol) was dissolved in DMF (2750 μL) followed by addition of m7GDP (1882 $mOD_{260\ nm}$, 99 mg, 165 μmol) and anhydrous $ZnCl_2$ (225 mg, 1651 μmol). The mixture was stirred at room temperature for 1 h and then the reaction was quenched by addition of a solution of $Na_2EDTA$ (676 mg) and $NaHCO_3$ (338 mg) in water (27.5 mL). The product was isolated by ion-exchange chromatography on DEAE Sephadex (gradient elution 0-1.2 M TEAB) and purified by RP HPLC (C18) using a linear gradient of acetonitrile in aqueous $CH_3COONH_4$ buffer pH 5.9 to yield (after evaporation and repeated freeze-drying from water) an ammonium salt of $m^7Gppp^{Bn6}A_m pGpG$ (2151$mOD_{260\ nm}$, 53.2 μmol, 27%). The yield was estimated by UV absorption at 260 nm, assuming the extinction coefficient ε=40.5 L/mmol/cm).

$m^7Gppp^{Bn6}A_m pGpG$: RP-HPLC (gradient elution 0-50% MeOH in $CH_3COONH_4$ pH 5.9 in 7.5 min, then isocratically): $R_t$=7.840 min; HRMS ESI(−): m/z 1579.24313 (calcd. for $C_{49}H_{60}N_{20}O_{31}P_5^-$ [M-H]$^-$ 1579.24269); $^1H$ NMR (500 MHz, $D_2O$, TMS, 70° C.) δ=9.55 (s, 1H), 8.96 (s, 1H), 8.72 (s, 1H), 8.55 (s, 1H), 8.53 (s, 1H), 7.92-7.76 (m, 6H), 6.50 (d, J=6.2 Hz, 1H), 6.39 (d, J=4.1 Hz, 1H), 6.33 (d, J=5.4 Hz, 1H), 6.28 (d, J=5.9 Hz, 1H), 5.42-5.31 (m, 5H), 5.30-5.25 (m, 1H), 5.18 (t, J=5.3 Hz, 1H), 5.10 (t, J=4.6 Hz, 1H), 4.98-4.88 (m, 6H), 4.73-4.61 (m, 7H), 4.51 (s, 3H), 3.82 (s, 3H) ppm; $^{31}P$ NMR {1H} (203 MHz, $D_2O$, $H_3PO_4$, 70° C.) δ=0.82 (s, 1P), 0.40 (s, 1P), −10.06 (d, J=19.0, 1P), −10.18 (d, J=18.4 Hz, 1P), −21.52 (dd, J=19.0, 18.4 Hz) ppm;

Example 7: Preparation of Capped mRNA by In Vitro Transcription Method mRNAs encoding *Gaussia* luciferase were generated on template of pJET_T7_Gluc_128A plasmid digested with restriction enzyme AarI (ThermoFisher Scientifics). The plasmid was obtained by cloning the T7 promoter sequence and coding sequence of *Gaussia* luciferase into pJET_luc_128A.[13] Typical in vitro transcription reaction (20 μl) was incubated at 37° C. for 2 h and contained: RNA Pol buffer (40 mM Tris-HCl pH 7.9, 10 mM $MgCl_2$, 1 mM DTT, 2 mM spermidine), 10 U/μl T7 RNA polymerase, 1 U/μl RiboLock RNase Inhibitor, 2 mM ATP/CTP/UTP, 0.5 mM GTP, 3 mM cap analog of interest and 50 ng/μl digested plasmid as a template. Following 2 h incubation, 1 U/μl DNase I was added and incubation was continued for 30 min at 37° C. The crude mRNAs were purified with NucleoSpin RNA Clean-up XS (Macherey-Nagel). Quality of transcripts was checked on native 1.2% 1×TBE agarose gel, whereas concentration was determined spectrophotometrically. To remove uncapped RNA, transcripts were treated with 5'-polyphosphatase (Epicentre) and Xrn1 (New England Biolabs). Briefly, mRNAs were incubated with 5'-polyphosphatase (20 U/5 μg of mRNA) in dedicated buffer for 30 min at 37° C., then mRNAs were purified with NucleoSpin RNA Clean-up XS. Purified mRNAs were subjected to incubation with Xrn-1 (1 U/1 μg of mRNA) in dedicated buffer for 60 min at 37° C., then mRNAs were purified with NucleoSpin RNA Clean-up XS.

Example 8: Purification of Capped mRNA Using HPLC

Transcripts were purified using Agilent Technologies Series 1200 HPLC, for which the RNASep™ Prep-RNA Purification Column (ADS Biotec) was used. The separation was carried out at 55° C. as described in [14]. A linear gradient of 35% to 55% buffer B (0.1 M triethylammonium acetate pH 7.0 and 25% acetonitrile) in buffer A (0.1 M triethylammonium acetate pH 7.0) at a flow rate of 0.9 ml/min for 22.1 min (gradient A) or 17.5% to 25.8% buffer C (0.1 M triethylammonium acetate, pH 7.0, and 50% acetonitrile) in buffer A (0.1 M triethylammonium acetate, pH 7.0) at a flow rate of 0.9 ml/min over 20 min (gradient B). The retention times of the mRNA according to the invention compared with uncapped mRNA of the same sequence or mRNA capped with reference analogs are summarized in Table 1. After purification, the mRNA molecules were recovered by precipitation with isopropanol from the collected fractions. The quality of the transcripts was checked on a native 1.2% 1×TBE agarose gel, and their concentration was determined spectrophotometrically.

Importantly, the use of the above-described purification procedure allowed in each case the separation of mRNAs encoding *Gaussia* luciferase possessing novel cap analogs ($m^7$GpppA*pG-RNA) from non-capped RNA of the same sequence (ppp-RNA). The retention time at which mRNA elution occurred depended on the type of substituent at the N6-adenosine position (Table 1). For example, using gradient A, the retention times of the $m^7Gppp^{Bn6}A_m$pG-RNAGluc and ppp-RNAGluc transcripts analyzed were 19.4 min for and 18.2 min, respectively.

TABLE 1

HPLC purification conditions for different mRNAs

| mRNA | Solvents | Retention time (min) |
|---|---|---|
| pppRNA | Gradient A | 18.20 |
| $m^7Gpppm^6A_m$pG-RNA | Gradient A | 18.29 |
| $m^7Gppp^{Bn6}$ApG-RNA | Gradient A | 19.40 |
| pppRNA | Gradient B | 14.00 |
| $m^7$GpppApG-RNA | Gradient B | 14.39 |
| $m^7GpppA_m$pG-RNA | Gradient B | 14.45 |
| $m^7Gppp^{Bn6}$ApG-RNA | Gradient B | 15.56 |
| $m^7Gppp^{2MeBn6}$ApG-RNA | Gradient B | 15.43 |
| $m^7Gppp^{3MeBn6}$ApG-RNA | Gradient B | 15.96 |
| $m^7Gppp^{4MeBn6}$ApG-RNA | Gradient B | 15.59 |
| $m^7Gppp^{4FBn6}$ApG-RNA | Gradient B | 15.11 |
| $m^7Gppp^{di3,4FBn6}$ApG-RNA | Gradient B | 15.38 |
| $m^7Gppp^{1Naphm}$ApG-RNA | Gradient B | 16.50 |
| $m^7Gppp^{2Naphm}$ApG-RNA | Gradient B | 16.58 |
| $m^7Gppp^{5'S,BnB}$ApG-RNA | Gradient B | 15.10 |

Example 9: Protein Expression Analysis

3T3-L1 (murine embryo fibroblast-like cells, ATCC CL-173) were grown in DMEM (Gibco) supplemented with 10% FBS (Sigma), GlutaMAX (Gibco) and 1% penicillin/streptomycin (Gibco) at 5% $CO_2$ and 37° C. Murine immature dendritic cell line JAWS II (ATCC CRL-1 1904) was grown in RPMI 1640 (Gibco) supplemented with 10% FBS, sodium pyruvate (Gibco), 1% penicillin/streptomycin and 5 ng/ml GM-CSF (PeproTech) at 5% $CO_2$ and 37° C. In a typical experiment, $10^4$ of JAWS II cells and $4 \cdot 10^3$ of 3T3-L1 cells were seeded at the day of transfection in 100 μl medium without antibiotics per well of 96-well plate. Cells in each well were transfected for 16 h using a mixture of 0.3 μl Lipofectamine MessengerMAX Transfection Reagent (Invitrogen) and 25 ng mRNA in 10 μl Opti-MEM (Gibco). In order to assess *Gaussia* luciferase expression at multiple time points, medium was fully removed and replaced with the fresh one at each time point. To detect luminescence from *Gaussia* luciferase, 50 μl of 10 ng/ml h-coelenterazine (NanoLight) in PBS was added to 10 μl of cell cultured medium and the luminescence was measured on Synergy H1 (BioTek) microplate reader.

CONCLUSIONS

Examples 1-6 describe methods for preparing tri- and tetranucleotide cap analogs according to the invention. Realizations of the invention, the synthesis of which has not been described in examples, can be executed by methods identical or very similar to those exemplified.

Examples 7 and 8 describe a method for the preparation and purification of mRNAs obtained with the use of compounds according to the invention, in conditions enabling separation of capped mRNAs from uncapped mRNAs.

FIG. 1 depicts representative chromatograms demonstrating such separation in comparison with corresponding results obtained for mRNAs obtained with an unmodified reference trinucleotide, which as demonstrated, does not enable separation of capped and uncapped mRNAs under the same conditions. Table 1 compares the chromatographic properties of mRNAs modified with different cap analogs. mRNAs modified with cap analogs according to the invention were eluted from the HPLC column at retention times longer than mRNAs not capped or terminated with reference cap analogs known from the state of the art. This indicates that the introduction of a suitably hydrophobic substituent at the N6-adenosine position facilitates purification of mRNA from uncapped contaminants. Moreover, analysis of the data shown in FIG. 1 (integration of the corresponding signals), enabled calculation of capping efficiency for mRNAs obtained with compound according to the invention, which was 91.5%. %. This indicates that when using the trinucleotide analogues of the cap according to the invention, it is possible to obtain capping efficiencies comparable to the trinucleotides without the modification according to the invention, for which the capping efficiencies obtained in the literature under similar conditions were about 90% [12].

Example 9 describes the method of analyzing protein expression in mammalian cells from mRNAs according to the invention obtained with compounds according to the invention. The analysis was performed in two cell lines representing cells from different origins (fibroblasts—3T3-L1 and dendritic cells—JAWS II). In the case of mRNAs obtained with the use of compounds according to the invention, enzymatic treatment was not performed because it was redundant.

mRNA obtained with the use of compounds according to the invention showed increased protein expression levels in comparison with mRNA obtained with cap analogs representing the state-of-the-art in at least one of the tested experimental variants.

Achieving increased protein expression has a lot of applications in biotechnology and production of biopharmaceutics (production of human recombinant proteins) as well as in mRNA-based gene therapies. Increased protein expression in dendritic cells is particularly beneficial in the case of application in therapeutic anti-cancer vaccines.[15]

Increased protein expression in cells derived from other tissues (e.g. lungs, liver, other organs) is particularly beneficial in the case of application in gene replacement therapies.[16]

One can expect that achieving the therapeutic effect for the mRNAs according to the invention will be possible at lower doses compared to mRNAs obtained with state-of-the-art methods. Lowering the mRNA dose entails lower risk of side effects associated with toxicity of therapeutic mRNA, and thereby, increases the probability of therapeutic success. Moreover, one can expect that preparation of mRNA with the use of compounds according to the invention will enable production of mRNAs devoid of undesired mRNA triphosphate impurities.

REFERENCES

1. Moore, M., From birth to death: The complex lives of eukaryotic mRNAs. *Science* 2005, 309 (5740), 1514-1518.
2. Ziemniak, M.; Strenkowska, M.; Kowalska, J.; Jemielity, J., Potential therapeutic applications of RNA cap analogs. *Future Medicinal Chemistry* 2013, 5 (10), 1141-1172.
3. Grudzien-Nogalska, E.; Stepinski, J.; Jemielity, J.; Zuberek, J.; Stolarski, R.; Rhoads, R. E.; Darzynkiewicz, E., Synthesis of anti-reverse cap analogs (ARCAs) and their applications in mRNA translation and stability. *Translation Initiation: Cell Biology, High-Throughput Methods, and Chemical-Based Approaches* 2007, 431, 203-227.
4. Sahin, U.; Kariko, K.; Tureci, O., mRNA-based therapeutics—developing a new class of drugs. *Nature Reviews Drug Discovery* 2014, 13 (10), 759-780.
5. Stepinski, J.; Waddell, C.; Stolarski, R.; Darzynkiewicz, E.; Rhoads, R. E., Synthesis and properties of mRNAs containing the novel “anti-reverse” cap analogs 7-methyl (3'-O-methyl)GpppG and 7-methyl(3'-deoxy)GpppG. *Rna-a Publication of the Rna Society* 2001, 7 (10), 1486-1495.
6. Jemielity, J.; Fowler, T.; Zuberek, J.; Stepinski, J.; Lewdorowicz, M.; Niedzwiecka, A.; Stolarski, R.; Darzynkiewicz, E.; Rhoads, R. E., Novel “anti-reverse” cap analogs with superior translational properties. *Rna-a Publication of the Rna Society* 2003, 9 (9), 1108-1122.
7. Jemielity, J.; Kowalska, J.; Rydzik, A. M.; Darzynkiewicz, E., Synthetic mRNA cap analogs with a modified triphosphate bridge—synthesis, applications and prospects. *New Journal of Chemistry* 2010, 34 (5), 829-844.
8. Grudzien-Nogalska, E.; Jemielity, J.; Kowalska, J.; Darzynkiewicz, E.; Rhoads, R. E., Phosphorothioate cap analogs stabilize mRNA and increase translational efficiency in mammalian cells. *Rna-a Publication of the Rna Society* 2007, 13 (10), 1745-1755.
9. Kuhn, A. N.; Diken, M.; Kreiter, S.; Selmi, A.; Kowalska, J.; Jemielity, J.; Darzynkiewicz, E.; Huber, C.; Tureci, O.; Sahin, U., Phosphorothioate cap analogs increase stability and translational efficiency of RNA vaccines in immature dendritic cells and induce superior immune responses in vivo. *Gene Therapy* 2010, 17(8), 961-971.
10. Grudzien, E.; Kalek, M.; Jemielity, J.; Darzynkiewicz, E.; Rhoads, R. E., Differential inhibition of mRNA degradation pathways by novel cap analogs. *Journal of Biological Chemistry* 2006, 281 (4), 1857-1867.
11. Sikorski, Pawel J; Warminski, Marcin; Kubacka, Dorota; Ratajczak, Tomasz; Nowis, Dominika; Kowalska, Joanna; Jemielity, Jacek; The identity and methylation status of the first transcribed nucleotide in eukaryotic mRNA 5' cap modulates protein expression in living cells. *Nucleic Acids Research* 2020, 305-1048.
12. J. Kowalska, M. Lewdorowicz, J. Zuberek, E. Grudzien-Nogalska, E. Bojarska, J. Stepinski, R. E. Rhoads, E. Darzynkiewicz, R. E. Davis, J. Jemielity, *RNA* 2008, 14, 1119-1131.
13. M. Warminski, P. J. Sikorski, Z. Warminska, M. Lukaszewicz, A. Kropiwnicka, J. Zuberek, E. Darzynkiewicz, J. Kowalska, J. Jemielity, *Bioconjugate Chemistry* 2017, 28, 1978-1992.
14. D. Weissman, N. Pardi, H. Muramatsu, K. Karikó, *Methods Mol Biol* 2013, 969, 43-54.
15. Norbert Pardi, Michael J. Hogan, Frederick W. Porter, Drew Weissman, N. Nature Reviews Drug Discovery vol. 17, 261-279 (2018).
16. Berraondo P, Martini P G V, Avila M A, et al Messenger RNA therapy for rare genetic metabolic diseases Gut 2019; 68:1323-1330.
17. Anna Maria Rydzik et. al., Organic & Biomolecular Chemistry, issue 22, 2009.
18. M. Kalek et al., Bioorganic & Medicinal Chemistry, Vol. 14, Issue 9, 1 May 2006, Pages 3223-3230.
19. J. Kowalska et. al. (2009), Phosphoroselenoate Dinucleotides for Modification of mRNA 5' End. ChemBioChem, 10: 2469-2473.
20. J. Kowalska, et. al., Nucleic Acids Research, Volume 42, Issue 16, 15 Sep. 2014, Pages 10245-10264.
21. A. Rydzik et. al., Nucleic Acids Research, Volume 45, Issue 15, 6 Sep. 2017, Pages 8661-8675.

The invention claimed is:

1. A compound of formula:

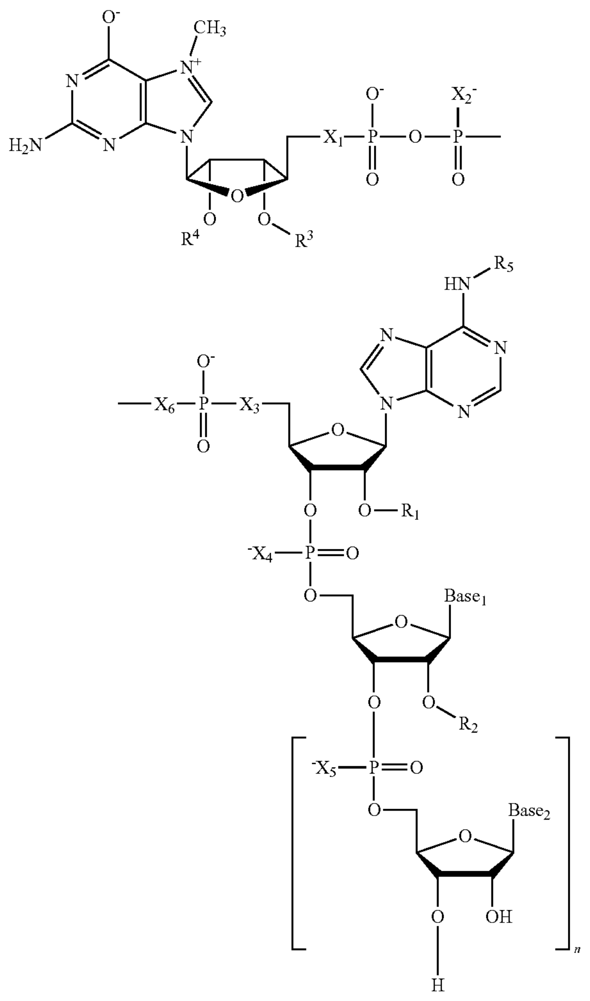

wherein:

$R_1$, $R_2$, $R_3$ and $R_4$ are selected from the group consisting of: H, $CH_3$ and alkyl, where R substituents with different numbers may be the same or different, n is 0 or 1, $R_5$ is selected from the group consisting of: benzyl, substituted benzyl, 1-naphthylmethyl, 2-naphtylmethyl, substituted naphthylmethyl, alkylaryl, aryl, $Base_1$ and $Base_2$ are independently selected from the group consisting of:

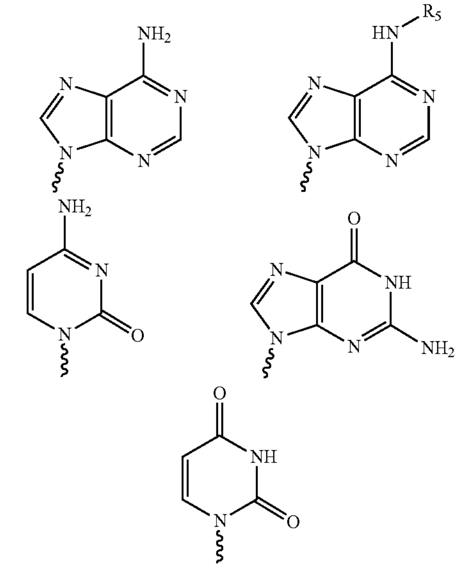

$X_1$ and $X_3$, are selected from the group consisting of: O, S, Se, whereby X substituents with different numbers may be the same or different, $X_2$, $X_4$ and $X_5$ are selected from the group consisting of: O, S, Se, $BH_3$, wherein X substituents with different numbers can be the same or different, $X_6$ is selected from the group consisting of: O, $CH_2$, $CF_2$, $CCl_2$.

2. A compound according to claim 1, wherein said compound is selected from the group consisting of:

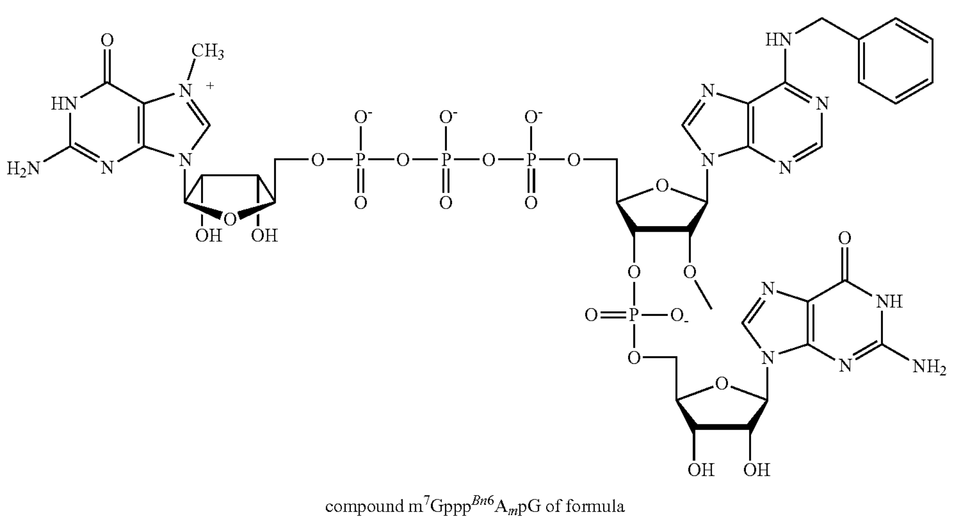

compound $m^7Gppp^{Bn6}A_mpG$ of formula

-continued
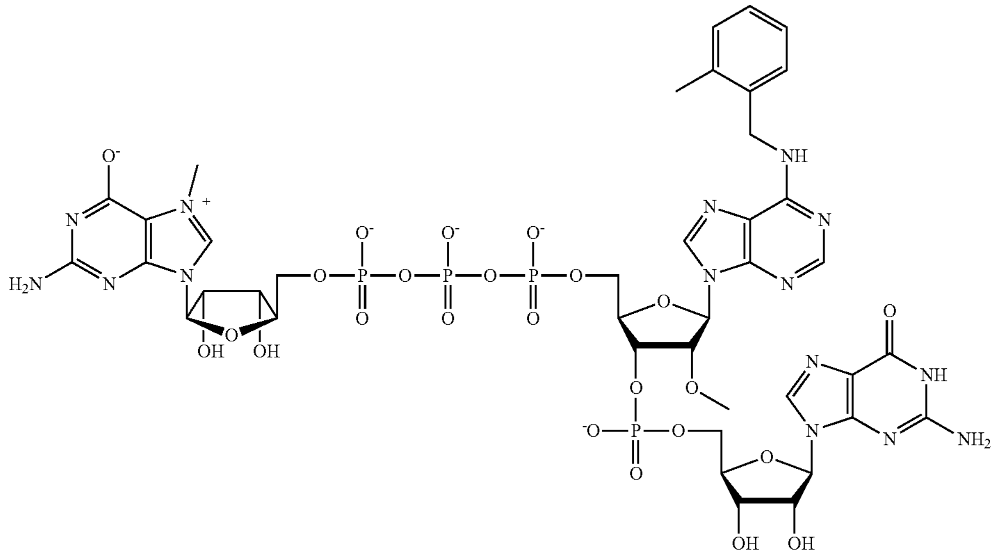
compound m$^7$Gppp$^{2MeBn6}$A$_m$pG of formula
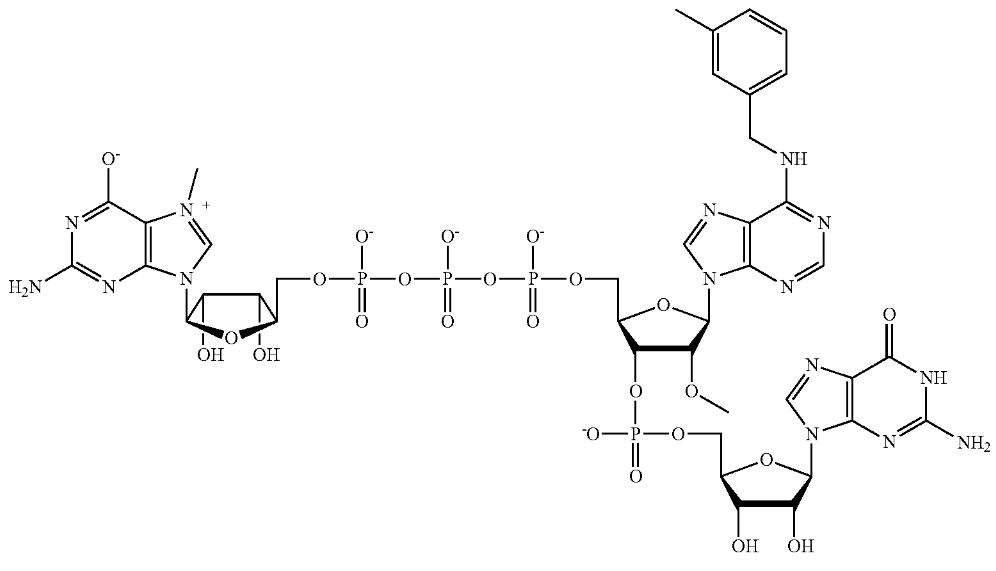
compound m$^7$Gppp$^{3MeBn6}$A$_m$pG of formula -continued
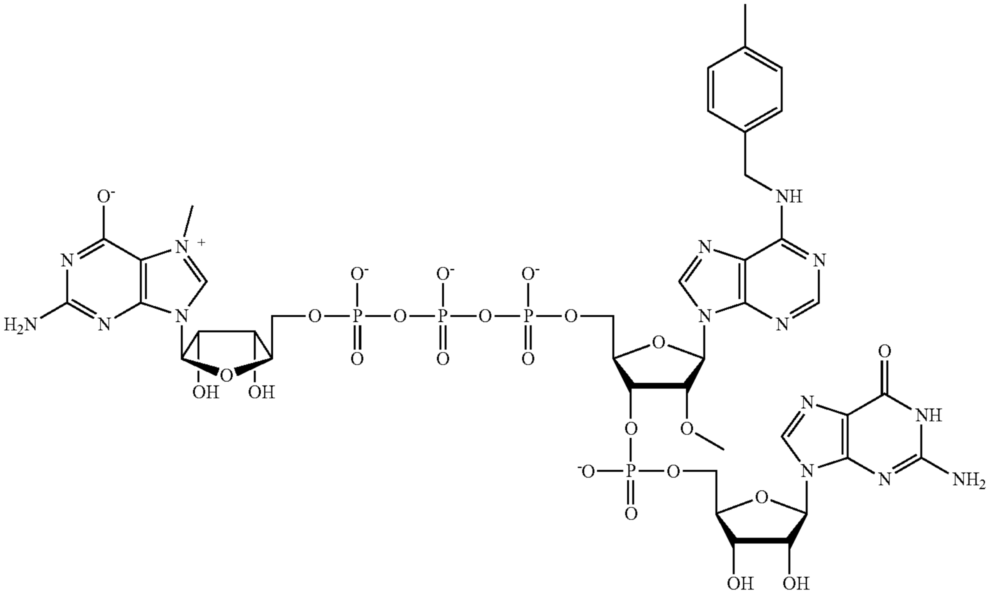
compound $m^7Gppp^{4MeBn6}A_mpG$ of formula
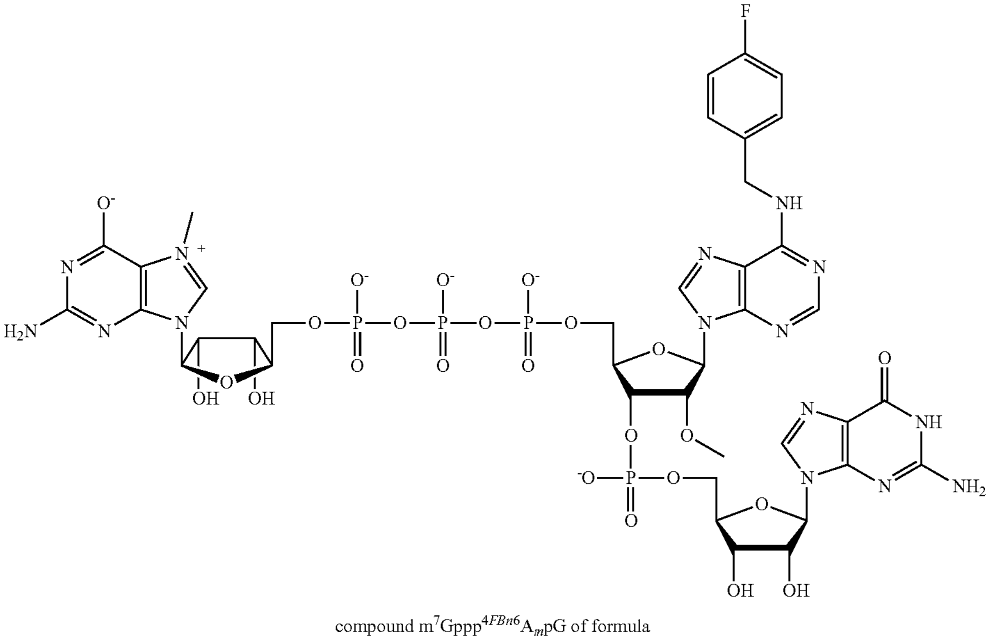
compound $m^7Gppp^{4FBn6}A_mpG$ of formula -continued
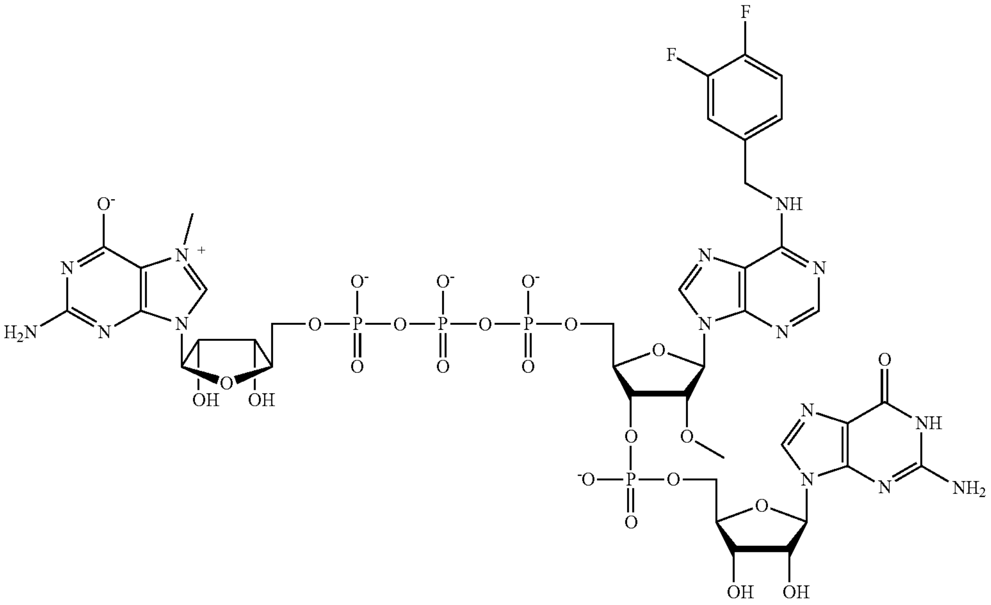
compound m⁷Gppp$^{3,4diFBn6}$A$_m$pG of formula
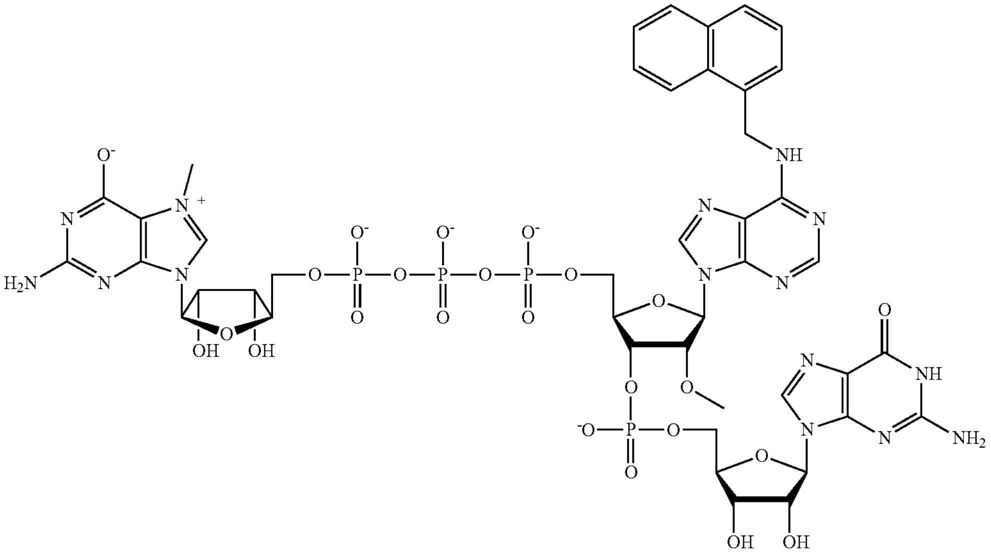
compound m$^7$Gppp$^{1Naphm6}$A$_m$pG of formula -continued
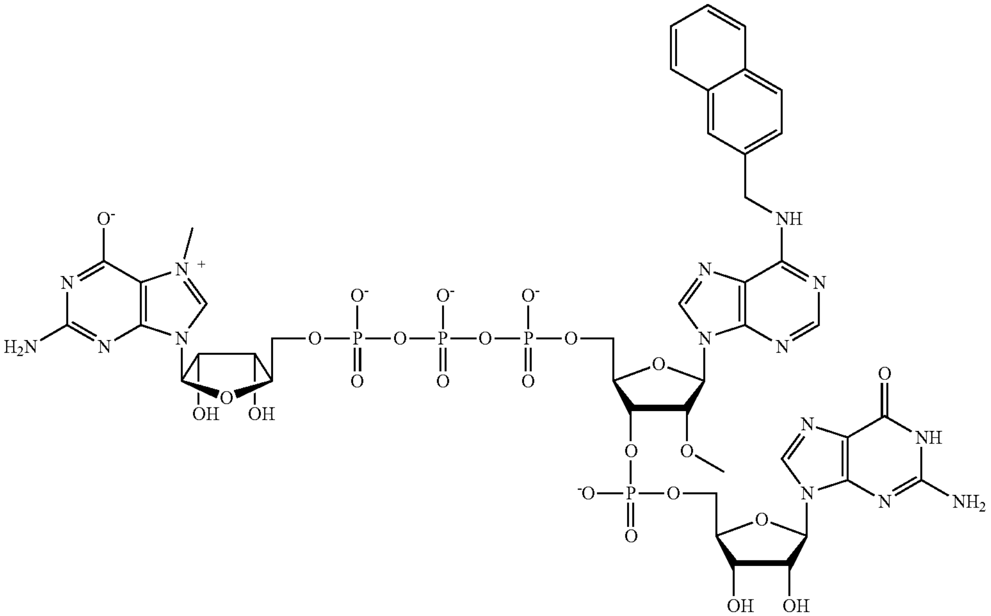
compound m$^7$Gppp$^{2Naphm6}$A$_m$pG of formula
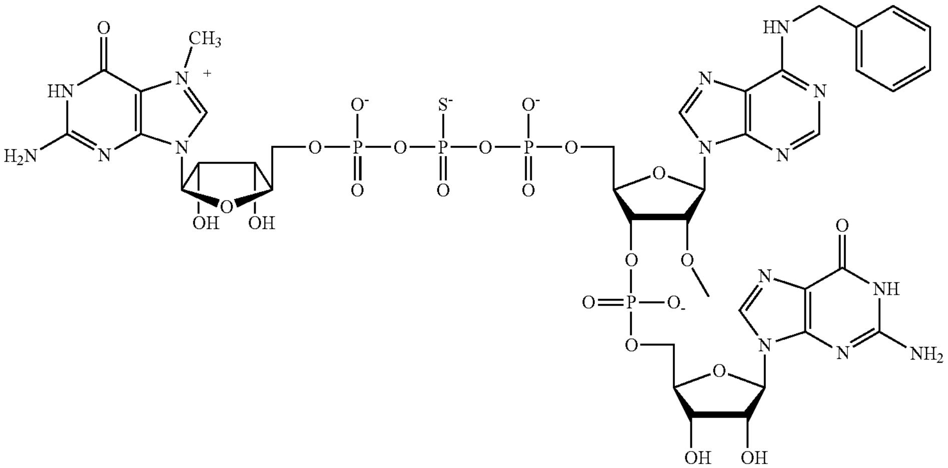
compound m$^7$Gpp$_S$p$^{Bn6}$A$_m$pG of formula -continued

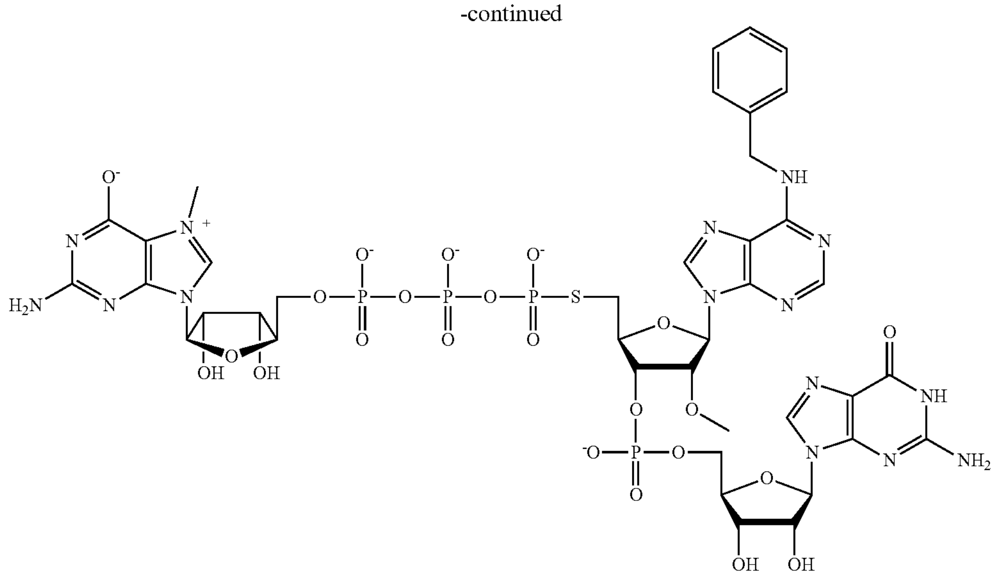

compound m$^7$Gppp$^{5'S,Bn6}$A$_m$pG of formula

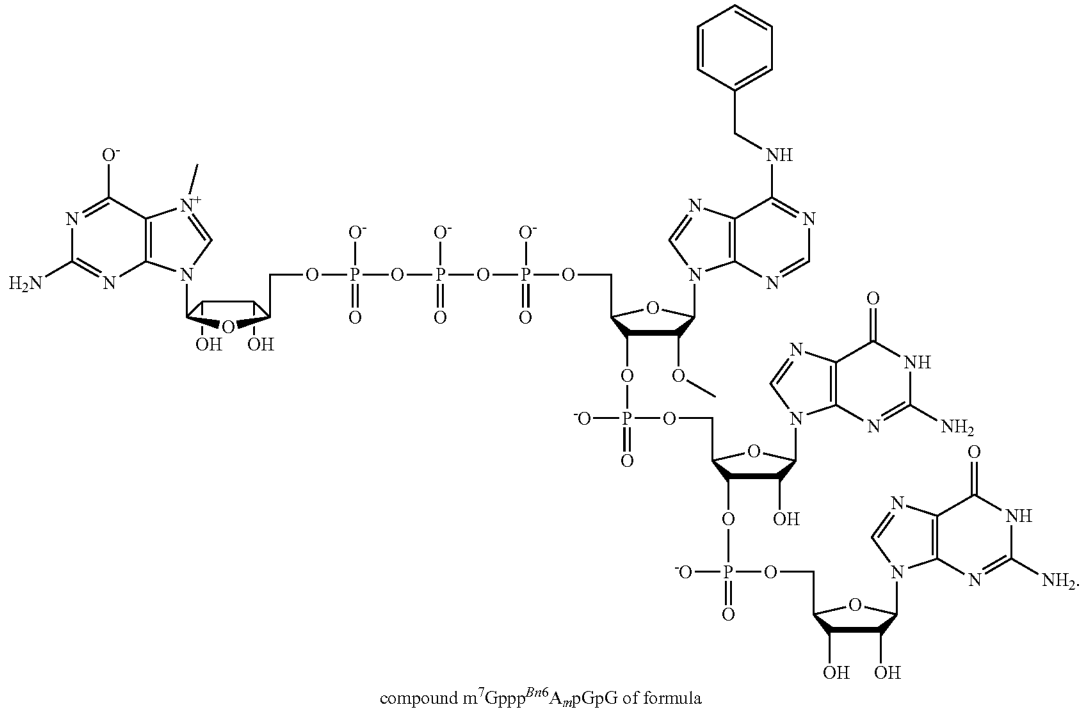

compound m$^7$Gppp$^{Bn6}$A$_m$pGpG of formula

3. A compound according to claim 1, wherein said compound consists essentially of a single stereoisomer or comprises a mixture of at least two stereoisomers, the first diastereomer and the second diastereomer, wherein the diastereomers are otherwise identical, except that they have different stereochemical configurations around the stereogenic phosphorus atom, wherein a stereogenic phosphorus atom is attached to a sulfur atom, selenium atom, or borane group.

4. A compound according claim 1, wherein $R_5$ is mono- or disubstituted benzyl.

5. A compound according claim 1, wherein $R_5$ is benzyl substituted with chlorine, fluorine, bromine, iodine, methyl, alkyl, nitro group, carboxyl group, azide group, amine group, hydroxyl group or a combination thereof.

6. A compound according claim 1, wherein $R_5$ is benzyl, monosubstituted benzyl, disubstituted benzyl, 1-napthylmethyl or 2-naphtylmethyl.

7. A compound according claim 1, wherein $X_1$, $X_4$, $X_5$, $X_6$ are O.

8. A compound according claim 1, wherein $X_2$ and $X_3$ are O or S.

9. A compound according claim 1, wherein $R_3$ and $R_4$ are H.

10. An RNA molecule whose 5' end incorporates the compound as defined in claim 1.

11. A method for synthesizing at least one RNA molecule in vitro; said method comprising reacting ATP, CTP, UTP, GTP, a compound as defined in claim 1, and a polynucleotide template in the presence of RNA polymerase, under conditions conducive to transcription by the RNA polymerase of the polynucleotide template into an RNA copy; wherein at least one of the RNA copies will incorporate the compound to make at least one RNA molecule that has said compound at the 5'end.

12. An in vitro protein or peptide synthesis method, said method comprising translating the RNA molecule according to claim 10, in a cell-free protein synthesis system, wherein the RNA molecule comprises an open reading frame, under conditions conducive to translating the open reading frame of the RNA molecule into the protein or peptide encoded by the open reading frame.

13. A method for synthesizing a protein or peptide in living cell, said method comprising introducing an RNA molecule as defined in claim 10 into cells, wherein the RNA molecule comprises an open reading frame, under conditions conducive to translating the open reading frame of the RNA molecule into the protein or peptide encoded by the open reading frame, wherein said cell is not contained in patient's body.

14. A method of purifying a molecule as defined in claim 10, wherein said method comprises using a chromatographic column, whereby the column is equilibrated, a sample containing said molecule is introduced onto the chromatographic column, the components of the sample are separated in a buffered aqueous solution/organic solvent system, and the fractions containing the molecule are collected, wherein mRNA molecule is separated from other RNA molecules that do not have said compound at the 5' end.

* * * * *